(12) United States Patent
Anderson et al.

(10) Patent No.: US 11,255,866 B2
(45) Date of Patent: Feb. 22, 2022

(54) METHODS FOR PREDICTING GLUCOREGULATORY DYSFUNCTION VIA DIACYLGLYCEROL FATTY ACID SPECIES CONCENTRATIONS

(71) Applicant: Wisconsin Alumni Research Foundation, Madison, WI (US)

(72) Inventors: Rozalyn M. Anderson, Madison, WI (US); Dhanansayan Shanmuganayagam, Madison, WI (US); Ricki L. Colman, Cross Plains, WI (US); James Mukasa Ntambi, Fitchburg, WI (US); Mary J. Lindstrom, Madison, WI (US); Michael A. Polewski, Madison, WI (US); Maggie S. Burhans, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/546,526

(22) PCT Filed: Feb. 25, 2016

(86) PCT No.: PCT/US2016/019509
§ 371 (c)(1),
(2) Date: Jul. 26, 2017

(87) PCT Pub. No.: WO2016/138232
PCT Pub. Date: Sep. 1, 2016

(65) Prior Publication Data
US 2018/0052182 A1 Feb. 22, 2018

Related U.S. Application Data

(60) Provisional application No. 62/121,165, filed on Feb. 26, 2015.

(51) Int. Cl.
*G01N 33/92* (2006.01)
*G06Q 40/08* (2012.01)

(52) U.S. Cl.
CPC ............ *G01N 33/92* (2013.01); *G06Q 40/08* (2013.01); *G01N 2800/04* (2013.01);
(Continued)

(58) Field of Classification Search
CPC ............... G01N 33/92; G01N 2405/00; G01N 2405/02; G01N 2800/042
See application file for complete search history.

(56) References Cited

U.S. PATENT DOCUMENTS

2005/0282897 A1   12/2005  Vanden Heuvel et al.
2010/0163720 A1*  7/2010  Bethan ............... G01N 33/6848
                                                        250/282

(Continued)

FOREIGN PATENT DOCUMENTS

EP          2503339 A1     9/2012

OTHER PUBLICATIONS

Jove, M. et al. "Plasma lipidomics discloses metabolic syndrome with a specific HDL phenotype," FASEB J. 2014 28(12):5163-5171, Published online Aug. 28, 2014. (Year: 2014).*

(Continued)

*Primary Examiner* — Christopher Adam Hixson
*Assistant Examiner* — Michelle Adams
(74) *Attorney, Agent, or Firm* — McDonnell Boehnen Hulbert & Berghoff LLP

(57) ABSTRACT

Provided herein are reagents, methods and biochemical markers for identifying individuals with glucoregulatory dysfunction and providing therapeutic intervention for individuals identified as at risk for glucoregulatory dysfunction. Specifically provided herein are methods for identifying a subject with glucoregulatory dysfunction based on changes (Continued)

in fasting blood lipid concentrations including, inter alia, diacylglycerols.

7 Claims, 15 Drawing Sheets

(52) U.S. Cl.
CPC . *G01N 2800/042* (2013.01); *G01N 2800/044* (2013.01); *G01N 2800/50* (2013.01); *G01N 2800/52* (2013.01)

(56) References Cited

U.S. PATENT DOCUMENTS

| | | | |
|---|---|---|---|
| 2010/0197028 A1* | 8/2010 | Watkins | G01N 33/6893 436/67 |
| 2014/0066508 A1 | 3/2014 | Yang et al. | |

OTHER PUBLICATIONS

Pehowich, D.J. "Dietary n-3 fatty acids alter angiotensin-induced contraction and 1,2-diacylglycerol fatty acid composition in thoracic aortas from diabetic rats," Prostaglandins, Leukotrienes and Essential Fatty Acids (1998) 58(4), 301-309. (Year: 1998).*
Hotamisligil,GS, "Inflammation and metabolic disorders," Nature, 444:860-867 (2006).
Bremer, et al., "Adipose Tissue Dysfunction in Nascent Metabolic Syndrome," Journal of Obesity, 2013:393192 (2013).
Ramsey, et al., "Dietary restriction and aging in rhesus monkeys: the University of Wisconsin study," Exp. Gerontol, 35:1131-1149 (2000).
Ramsey, et al., "Age and gender differences in body composition, energy expenditure, and glucoregulation of adult rhesus monkeys," J. Med Primatol 29:11-19 (2000).
Gresl, et al., "Dietary restriction and glucose regulation in aging rhesus monkeys: A follow-up report at 8.5 years," Am J. Physiol Endocrinol Metal, 281:E757-765 (2001).
Hudson, et al., "Age and sex differences in body size and composition during rhesus monkey adulthood," Aging (Milano) 8:197-204 (1996).
Raman, et al., "Reference Body Composition in Adult Rhesus Monkeys: Glucoregulatory and Anthropometric Indices," J. Gerontol A. Biol Sci Med Sci., 60:1518-1524 (2005).
Uno, "Age-Related Pathology and Biosenescent Markers in Captive Rhesus Macaques," Age (Omaha) 20:1-13 (1997).
Fischer KE, et al., "The development of small primate models for aging research," ILAR J 52:78-88 (2011).
Ding, et al., "Nuclear magnetic resonance-determined lipoprotein abnormalities in nonhuman primates with the metabolic syndrome and type 2 diabetes mellitus," Metabolism, 56:838-846 (2007).
Kemnitz, "Obesity in male and female rhesus monkeys: fat distribution, glucoregulation, and serum androgen levels," J. Clin Endocrinol Metab., 69:287-293 (1989).
Clement, K., et al., "Regulation of inflammation-related genes in human adipose tissue," J. Intern Med., 262:422-430 (2007).
Das, et al., "Caloric restriction, body fat and ageing in experimental models," Obesity Reviews, 5:13-19 (2004).
Kirkland, et al., "Adipogenesis and aging: does aging make fat go MAD?" Experimental Gerontology, 37:757-767 (2002).
Bligh, et al., "A Rapid method of Total Lipid Extraction and Purification," Canadian J. Biochem Physiol 37:911-917 (1959).
Taksali, et al., "High Visceral and Low Abdominal Subcutaneous Fat Stores in the Obese Adolescent," Diabetes, 57:367-371 (2008).
Wisse, "The Inflammatory Syndrome: The Role of Adipose Tissue Cytokines in Metabolic Disorders Linked to Obesity," J. Am Soc Nephrol, 15:2792-2800 (2004).
Samuel & Shulman, "Mechanisms for Insulin Resistance: Common Threads and Missing Links," Cell, 148:852-871 (2012).
Rohrer, et al., "High density lipoproteins in the intersection of diabetes mellitus, inflammation and cardiovascular disease", Curr. Opin Lipidol, 15:269-278 (2004).
Chapman, "Metabolic syndrome and type 2 diabetes: lipid and physiological consequences.," Diab Vase Dis Res 4 Suppl 3:S5-8(2007).
Kontush & Chapman, "Functionally Defective High-Density Lipoprotein: A New Therapeutic Target at the Crossroads of Dyslipidemia, Inflammation, and Atherosclerosis," Pharmacol Rev, 58:342-374 (2006).
Lago, et al., "The emerging role of adipokines as mediators of inflammation and immune responses," Cytokine Growth Factor Rev., 18:313-325 (2007).
Ouchi, et al., "Adipokines in inflammation and metabolic disease," Nat. Rev Immunol 11:85-97 (2011).
Rosen & Spiegelman, "Adipocytes as regulators of energy balance and glucose homeostasis," Nature 444:847-853 (2006).
Tilg & Moschen, "Adipocytokines: mediators linking adipose tissue, inflammation and immunity." Nat Rev. Immuno., 6:772-783 (2006).
Turer & Scherer, "Adiponectin: mechanistic insights and clinical implications," Diabetologia, 55:2319-2326 (2012).
Turer, et al., "Adiponectin as an Independent Predictor of the Presence and Degree of Hepatic Steatosis in the Dallas Heart Study," J. Clin Endocrinol Metab, 97:E982-986 (2012).
Obata, et al., "Relationship between serum adiponectin levels and age in healthy subjects and patients with type 2 diabetes," Clinical Endocrinol (Oxf) 79:204-210 (2013).
Wolfson, et al., "Relation of Adiponectin to Glucose Tolerance Status, Adiposity, and Cardiovascular Risk Factor Load," Exp. Diabetes Res, 2012:250621 (2012).
Kim, et al., "Association of fatty acid composition in serum phospholipids with metabolic syndrome and arterial stiffness," Nutr. Metabol. Cardiovasc. Dis., 23:366-374 (2013).
Mayneris-Perxachs, et al., "Plasma fatty acid composition, estimated desaturase activities, and their relation with the metabolic syndrome in a population at high risk of cardiovascular disease," Clin. Nutr., 33:90-97 (2014).
Telle-Hansen, et al., "Substitution of TAG oil with diacyglycerol oil in food items improves the predicted 10 years cardiovascular risk score in healthy, overweight subjects," J. Nutr. Sci., 1:1-13 (2012).
Polewski, et al., "Plasma diacylglycerol composition is a biomarker of metabolic syndrome onset in rhesus monkeys," J. Lipid Res., 56:1461-1470 (2015).
International Search Report and Written Opinion for PCT/US2016/019509, pp. 1-17.

\* cited by examiner

METHODS FOR PREDICTING GLUCOREGULATORY DYSFUNCTION VIA DIACYLGLYCEROL FATTY ACID SPECIES CONCENTRATIONS

This invention was made with government support under RR025011, AG037000 and AG011915 awarded by the National Institutes of Health. The government has certain rights in the invention.

This application is a national stage application under 35 U.S.C. § 371 of International Application No. PCT/US2016/019509 filed Feb. 25, 2016, which claims the benefit of U.S. Provisional Patent Application Ser. No. 61/121,165, filed Feb. 26, 2015 the disclosures of which are explicitly incorporated by reference herein.

BACKGROUND OF THE INVENTION

Field of the Invention

This invention provides reagents, methods and biochemical markers for identifying individuals with glucoregulatory dysfunction and for determining efficacy of a therapeutic intervention to correct glucoregulatory dysfunction. The invention specifically provides methods for identifying a subject with glucoregulatory dysfunction based on changes in fasting blood lipid concentrations including, inter alia, diacylglycerols.

Description of Related Art

The term glucoregulatory dysfunction covers a spectrum of disorders with increasing severity from insulin resistance, to pre-diabetes, to frank diabetes. Glucoregulatory dysfunction is often first clinically identified by abnormally elevated fasting blood glucose levels (100-125 mg/dl) and/or abnormally elevated fasting blood glycosylated hemoglobin (HbA1c>5.7-6.4%), a condition known as Impaired Fasting Glucose or pre-diabetes. Pre-diabetes is secondary to existing insulin resistance; however, the diagnostic test to detect insulin resistance (elevated blood glucose [140-199 mg/dl] 2 hours following Oral Glucose Tolerance Test) is not generally conducted in the absence of evidence of elevated fasting blood glucose and/or HbA1c levels (i.e., it is a test to confirm rather than initially detect the presence of insulin resistance in a patient). In this way, insulin resistance in the absence of elevated fasting blood glucose frequently goes undetected. A method that could be routinely administered to detect insulin resistance in advance of changes in fasting blood glucose or HbA1c would allow much earlier detection of elevated risk for a range of conditions including metabolic syndrome, pre-diabetes, and Type II (or adult onset) diabetes, allowing for earlier intervention and improved patient outcomes.

Metabolic syndrome is an obesity related condition of increased vulnerability for a spectrum of diseases including diabetes (Hotamisligil, 2006, Nature 444: 860-867). Although obesity and glucoregulatory dysfunction dominate health care in the U.S. today, current assessments to identify risk for diabetes rely largely on body mass index (BMI), waist circumference, and family history. According to a 2010 U.S. Center for Disease Control (CDC) report, 69% of the U.S. adult population is overweight or obese and 85% of Type II diabetics are overweight or obese; however, only 10% of the overweight and obese are diabetic. This indicates that glucoregulatory dysfunction is exacerbated by obesity but suggests that the etiology may be more nuanced. One possibility is related to the endocrine nature of adipose tissue, where production of bioactive peptides and fatty acids rather than the expansion of adipose tissue in itself plays a role in disease vulnerability (Bremer & 2013, J Obes 2013: 393192). Currently, there are no biochemical markers that accurately predict which overweight/obese individuals are most likely to develop glucoregulatory dysfunction or glucoregulatory dysfunction associated with metabolic syndrome. Thus, there is a need in the art for reagents and methods for identifying individuals having a risk for glucoregulatory dysfunction that can be administered routinely and as a way to screen individuals for this risk before they have progressed to pre-diabetes.

SUMMARY OF THE INVENTION

This invention provides reagents, methods and biochemical markers for identifying and providing therapeutic intervention for individuals with a risk for glucoregulatory dysfunction. Specifically, provided herein are methods for identifying a subject at risk for glucoregulatory dysfunction, the method comprising (a) separating diacylglycerols from a biosample isolated from the subject; (b) determining a concentration of one or more diacylglycerol fatty acid species comprising the separated diacylglycerols; and (c) identifying the subject as having a risk for glucoregulatory dysfunction when the concentration of one or more diacylglycerol fatty acid species is increased or decreased relative to a control level or range.

In particular embodiments, the glucoregulatory dysfunction is associated with metabolic syndrome, pre-diabetes, or Type II (or adult onset) diabetes.

In further embodiments the methods comprise determining in the biosample a concentration of one or more lipoproteins, including very low-density lipoprotein, high-density lipoprotein, low-density lipoprotein, intermediate-density lipoprotein, and chylomicrons. In particular embodiments an increased concentration of very low density lipoprotein compared to a relative control level or range identifies a subject at risk for glucoregulatory dysfunction.

In particular embodiments a decreased concentration of high-density lipoprotein compared to a relative control level or range identifies a subject at risk for glucoregulatory dysfunction.

In other aspects the invention provides methods for identifying a subject that is eligible for reimbursement of an insurance claim for treatment of glucoregulatory dysfunction. These methods comprise (a) separating diacylglycerols from a biosample isolated from the subject; (b) determining the level of one or more diacylglycerol fatty acid species within the biosample; and (c) identifying the subject as eligible for reimbursement of the insurance claim when the concentration of one or more diacylglycerol fatty acid species is increased or decreased relative to an insurance control value.

In particular embodiments of the several methods of this invention, the concentration of one or more diacylglycerol fatty acid species is determined using gas chromatography. In other embodiments the biosample comprises serum or plasma from the subject.

In yet other particular embodiments the one or more diacylglycerol fatty acid species comprise fatty acids having a carbon chain between 12 to 20 carbons including saturated, monounsaturated, and polyunsaturated species, such as C16:1(n-7), C18:2 (n-6), C18:3(n-3) and C20:1(n-7). In particular embodiments a subject is identified as at risk for glucoregulatory dysfunction when the concentration of one or more of C16:1(n-7), C18:2 (n-6), C18:3(n-3) and C20:1(n-7) is decreased. In other embodiments a subject is identified as at risk for glucoregulatory dysfunction when the concentration of C18:2 (n-6) is increased.

In other aspects the invention provides methods for identifying a subject at risk for glucoregulatory dysfunction comprising (a) separating diacylglycerols from a biosample isolated from the subject; (b) determining the level of a diacylglycerol in the subject's biosample; and (c) identifying the patient as having a risk for glucoregulatory dysfunction when the concentration of the separated diacylglycerols is increased or decreased relative to a control level or range.

In particular embodiments the methods further comprise the step of intervening therapeutically to decrease the subject's risk of glucoregulatory dysfunction wherein the therapeutic intervention comprises administering to the subject an effective amount of at least one anti-diabetes compound, wherein the anti-diabetes compound is a compound or pharmaceutical composition effective against diabetes in a subject. In other embodiments the subject is identified as having a risk for glucoregulatory dysfunction within a sufficient time to allow for a therapeutic intervention to decrease the subject's risk of glucoregulatory dysfunction.

In other aspects methods for determining the efficacy of a treatment for glucoregulatory dysfunction are provided wherein the method comprises (a) separating diacylglycerols from a biosample isolated from a subject undergoing treatment for glucoregulatory dysfunction; (b) determining the concentration of one or more diacylglycerol fatty acid species comprising the separated diacylglycerols; and (c) determining the efficacy of the treatment for glucoregulatory dysfunction when the concentration of one or more diacylglycerol fatty acid species is increased or decreased relative to a pre-treatment level or range.

In other aspects provided herein are methods for detecting alterations in blood lipid chemistry involving diacylglycerol fatty acid species, the method comprising: (a) separating diacylglycerols from a biosample isolated from the subject; (b) determining a concentration of one or more diacylglycerol fatty acid species comprising the separated diacylglycerols; and (c) detecting alternations in blood lipid chemistry relative to a control level or range.

Specific preferred embodiments of the present invention will become evident from the following more detailed description of certain preferred embodiments and the claims.

BRIEF DESCRIPTION OF THE DRAWINGS

FIG. 1A is a schematic of study design, eight animals per group per time-point. FIG. 1B are graphs illustrating total body fat, percent body fat, abdominal fat, and abdominal circumference. FIG. 1C are graphs illustrating plasma leptin and resistin levels in metabolic impaired (Meti) and age- and weight-matched controls (Ctrl) at time of diagnosis (Dx) and two years prior to diagnosis (pre-Dx). FIG. 1D are graphs illustrating plasma total adiponectin and high molecular weight (HMW) adiponectin in metabolic impaired (Meti) and age- and weight-matched controls (Ctrl) at time of diagnosis (Dx) and two years prior to diagnosis (pre-Dx). Data are shown as medians and interquartile range (IQR).

FIG. 3A is a schematic representation of fatty acid chain elongation and saturation from palmitic acid (C16:0), or dietary linoleic acid (C18:2 (n-6)) and linolenic acid (C18:3(n-3)). FIG. 3B are graphs showing levels of significantly impacted DAG fatty acid species in metabolic impaired (Meti) and age- and weight-matched controls (Ctrl) at time of diagnosis (Dx) and two years prior to diagnosis (pre-Dx). FIG. 3C are graphs showing relative abundance of DAG fatty acids that together constitute a predictive model for metabolic syndrome risk. Data are shown as medians and IQR. *$p<0.05$ for control vs impaired.

FIG. 5A are graphs showing significant differences in plasma levels of HDL (high density lipoproteins), HLP (HDL large particles), IDLP (Intermediate density lipoproteins large particles), NHC (HDL cholesterol), HSP (HDL small particles) and triacylglycerol shown as medians and IQR in metabolic impaired (Meti) and age and weight matched controls (Ctrl) at time of diagnosis (Dx) and two years prior to diagnosis (pre-Dx). FIG. 5B illustrates positive and negative correlations for the indicated plasma lipoproteins and associated metrics with plasma concentrations of the following fatty acids in each class top to bottom and left to right in this order: C10:0, C12:0, C12:1, C14:0, C14:1, C16:0, C16:1, C18:0, C18:1(n-9), C18:1(n-7), C18: 2(n-6), C18:3(n-6), C18:3(n-3), C20:0, C20:1(n-9), C20:1 (n-7), C20:3(n-6), C20:4(n-6), C22:0, C22:5(n-3), saturated, MUFA, PUFA, total fatty acids. *$p<0.05$ control vs impaired, Δ*p value<0.05 for difference between the changes for impaired and control animals from two years prior to time of diagnosis.

FIG. 6A are graphs showing plasma levels of PL C18:0, PL C18:3(n-6), TG C14:0, and LDL large particles shown as medians and IQR in metabolic impaired (Meti) and age- and weight-matched controls (Ctrl) at time of diagnosis (Dx) and two years prior to diagnosis (pre-Dx). *$p<0.05$ control vs impaired, Δ*p value<0.05 for difference between the changes for impaired and control animals from two years prior to time of diagnosis. Without being bound by any particular theory or mechanistic formula or regime, FIG. 6B provides a schematic model for metabolic syndrome development based on the methods disclosed herein.

DETAILED DESCRIPTION OF THE INVENTION

Figure 1:
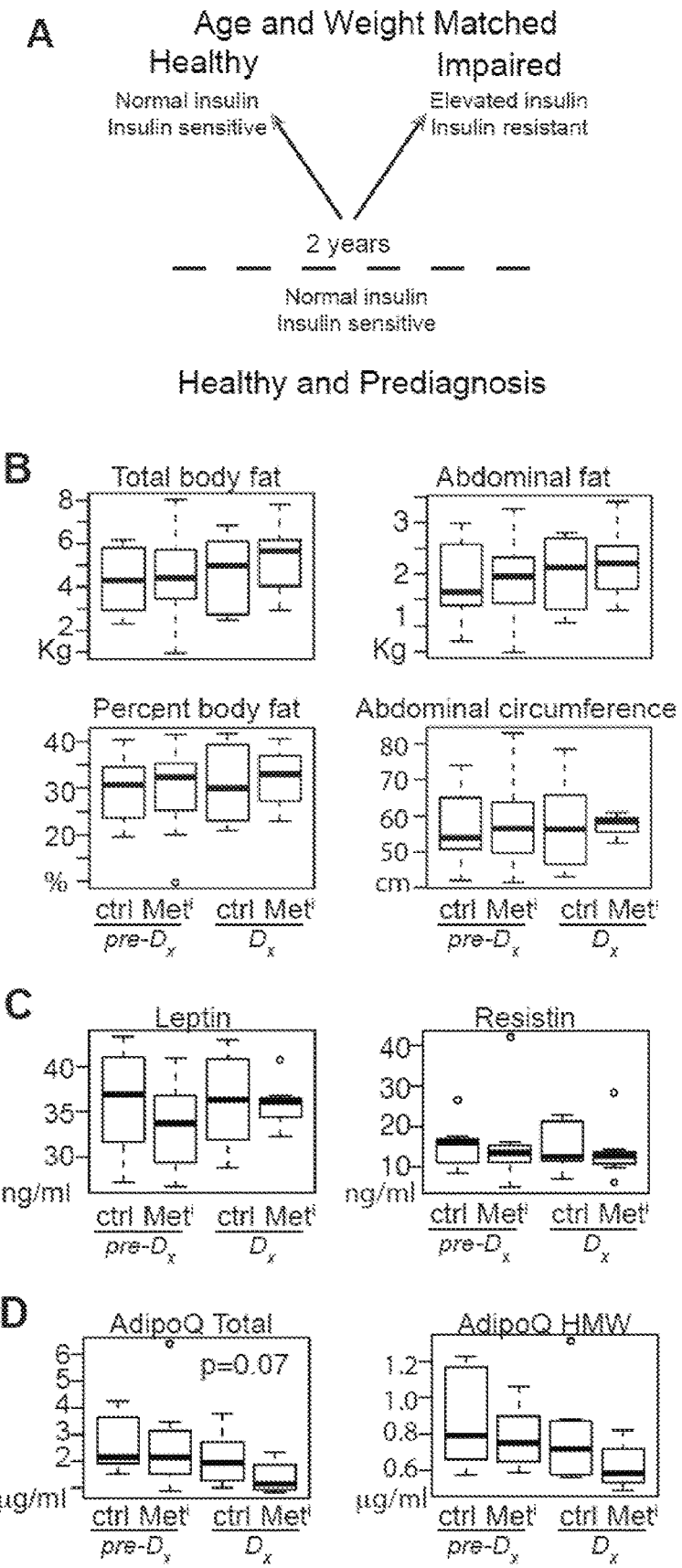
FIGS. 1A-1D illustrate that progression to metabolic syndrome in rhesus monkeys lowered adiponectin without a change in adiposity.

All publications, patents and patent applications cited herein are hereby expressly incorporated by reference for all purposes.

Provided herein are methods for identifying, preventing and/or treating a subject at risk for glucoregulatory dysfunction and its associated disorders. Glucoregulatory dysfunction will be recognized in the art as being characterized by fasting insulin greater than 25 μU/ml, and glucose levels between 140-199 mg/dl 2 hours following an Oral Glucose Tolerance Test (75 g bolus). Glucoregulatory dysfunction may include but is not limited to increased levels of fasting blood glucose (>100 mg/dl). Conditions associated with glucoregulatory dysfunction include metabolic syndrome, pre-diabetes, and Type II (or adult onset) diabetes.

As used herein "metabolic syndrome" refers to a patient that has three or more of a collection of indicators of aberrant metabolic homeostasis such as elevated fasting glucose or pre-diabetes, elevated triacylglycerols, high blood pressure, abdominal obesity, and low HDL cholesterol. Metabolic syndrome is a risk factor for cardiovascular diseases and Type II (or adult onset) diabetes that occur as a result of insulin resistance and an abnormal function and pattern of body fat. Disorders associated with metabolic syndrome include elevated diabetes risk, hypertension, obesity, abnormal lipid metabolism (e.g. dyslipidemia), central adiposity, oxidative stress and its many manifestations including, stroke, ischemia, and atherosclerosis.

In one particular aspect, provided herein are methods for identifying a subject at risk for glucoregulatory dysfunction, comprising (a) separating diacylglycerols from a biosample isolated from the subject; (b) determining a concentration of one or more diacylglycerol fatty acid species comprising the separated diacylglycerols; and (c) identifying the subject as having a risk for glucoregulatory dysfunction when the concentration of one or more diacylglycerol fatty acid species is increased or decreased to a control level or range.

As used herein "concentration" refers to both percent concentration and absolute concentration of a biomarker. "Percent concentration" refers to the comparative concentration of a biomarker with respect to another (i.e., the percent of total diacylglycerol fatty acid species detected). "Absolute concentration" refers to a direct measurement of the biomarker without comparison to other detected species (i.e., the concentration in the biosample of total diacylglycerol fatty acid species detected).

Separating lipids from a biosample and quantifying these lipids (e.g., determining their concentration), wherein "lipids" include but are not necessarily limited to cholesterol esters, free fatty acids, diacylglycerols, phospholipids and triglycerides, can be achieved using methods such as mass spectrometry (MS), high performance liquid chromatography (HPLC), isocratic HPLC, gradient HPLC, normal phase chromatography, reverse phase HPLC, size exclusion chromatography, ion exchange chromatography, capillary electrophoresis, microfluidics, chromatography, gas chromatography (GC), thin-layer chromatography (TLC), immobilized metal ion affinity chromatography (IMAC), affinity chromatography, immunoassays, and/or colorimetric assays. In particular embodiments the lipids are purified and isolated using thin layer chromatography. In other particular embodiments, the fatty acid composition of diacylglycerols is determined using gas chromatography.

The terms "diglyceride" and "diacylglycerol" are used herein interchangeably. A diacylglycerol is a glyceride consisting of two fatty acid chains covalently bonded to a glycerol molecule through ester linkages. Diacylglycerols can have many species of fatty acids varying in chain length and degree of saturation but are distinct from triglycerides because they comprise two rather than three fatty acids esterified to glycerol and also distinct from phosphoglycerides by the absence of a phosphate group esterified to the glycerol molecule comprising the glyceride.

The methods disclosed herein enable subjects having a risk for glucoregulatory dysfunction to be identified by detecting changes in circulating lipids in the early stages of glucoregulatory dysfunction. For example, changes in plasma diacylglycerols can be used to predict insulin resistance in overweight subjects and are a component of broad-scale changes in lipid metabolism that occur early during disease progression. In one embodiment, a subject is identified as having a risk for glucoregulatory dysfunction when the concentration of diacylglycerols in a biosample isolated from the subject is increased or decreased relative to a control (i.e., normal) level or range.

In another embodiment, the methods provided herein include measuring the concentration of diacylglycerol fatty acid species such as those having a carbon chain between 12 to 20 carbons, e.g., palmitoleic acid (also referred to by its lipid number of C16:1), linoleic acid (also referred to by its lipid number of C18:2 (n-6)), alpha-linolenic acid (also referred to by its lipid number of C18:3(n-3)) and paullinic acid (also referred to by its lipid number of C20:1 (n-7) or C20:1 (13-cis)). In particular embodiments the fatty acid species is C18:2 (n-6). Thus, changes in diacylglycerol relative composition can be the basis for a predictive model of metabolic syndrome (one embodiment thereof being shown in Table 2-Model 1).

Furthermore, glucoregulatory dysfunction subjects can exhibit patterns of fatty acid composition in a bodily fluid sample within the diacylglycerol class, fatty acids of cholesterol esters, and free fatty acid classes that can be used for predicting glucoregulatory dysfunction. For example, levels of an adipose tissue-derived systemic signaling peptide termed adiponectin, together with differences in plasma fatty acid chain length and degree of saturation can be used to predict insulin resistance as shown herein. Reduced levels of high-density lipoproteins can further be used to predict glucoregulatory dysfunction development in insulin-sensitive subjects. Distinct correlations for fatty acids within and among lipid classes can also be used for identifying or predicting a subject to be at risk for glucoregulatory dysfunction.

A "control level" as used herein refers to an amount or range of amounts of a biochemical marker such as a diacylglycerol or diacylglycerol fatty acid species found in a comparable biosample in subjects not suffering from glucoregulatory dysfunction, metabolic syndrome or Type II diabetes. The control level can also be based on a database of biochemical markers such as a diacylglycerol or diacylglycerol fatty acid species from previously tested subjects who did not convert to glucoregulatory dysfunction, metabolic syndrome or diabetes over a clinically relevant time.

The methods disclosed are advantageous for providing lipid-based predictions of insulin resistance in a subject independent of adiposity and in advance of changes in fasting blood glucose. The methods provided herein permit earlier therapeutic intervention directed towards delaying, reducing or preventing transition of a subject to glucoregulatory dysfunction. In particular embodiments the methods provided herein identify a subject as having risk for glucoregulatory dysfunction within a sufficient lead time to permit therapeutic intervention to decrease the subject's risk of metabolic syndrome or prevent the transition to metabolic syndrome and diabetes. Such therapeutic interventions can include, but are not limited to, exercise regimens, dietary modification, dietary supplementation, bariatric surgical intervention, and administration of pharmaceuticals such as an anti-diabetic compound, wherein the anti-diabetic compound is a compound or pharmaceutical composition effective against diabetes in a subject. The methods disclosed herein provide for a subject to be identified as being at risk for glucoregulatory dysfunction in advance of impaired fasting glucose (glucose range 100-125 mg/dl) or hyperglycemia (glucose>125 mg/dl).

The methods provided herein can be performed on a biosample isolated from a subject such as serum or plasma from blood. A "subject" as used herein can be, but not limited to, a human, non-human primate, mouse, rat, dog, cat, horse, pig, sheep or cow.

In particular embodiments, the disclosed methods are used to determine eligibility of a subject for medical insurance or reimbursement of a medical insurance claim, such methods comprising (a) separating diacylglycerols from a biosample isolated from the subject; (b) determining the level of one or more diacylglycerol fatty acid species within the biosample; (c) identifying the subject as eligible for reimbursement of the insurance claim when the concentration of one or more diacylglycerol fatty acid species is increased or decreased relative to an insurance control value.

The insurance control value refers to an amount or range of amounts of a biochemical marker such as a diacylglycerol or diacylglycerol fatty acid species found in a comparable biosample in subjects not suffering from glucoregulatory dysfunction such as metabolic syndrome or diabetes and used as an insurance reimbursement criterion by, inter alia, a health insurer. In another embodiment, insurance coverage of an individual is assessed as a function of actuarial data that is obtained from individuals with changes in concentration of measured fatty acid species. The control level can also be based on a database of biochemical marker such as a diacylglycerol or diacylglycerol fatty acid species from previously tested subjects who did not convert to glucoregulatory dysfunction, metabolic syndrome or diabetes over a clinically relevant time. Additionally, a control level could be based on an individual that did not file a reimbursement claim based on glucoregulatory dysfunction within an actuarially relevant time period.

In other embodiments, the subject is then included or enrolled in an insurance plan based on the insurable status of the subject or wherein the rate or cost of the insurance is based on the insurable status of the subject. Alternatively, the subject is then excluded from an insurance plan based on the insurable status of the subject. In some such instances, an organization that provides medical insurance requests or otherwise obtains information concerning a subject's biochemical marker status and uses that information to determine an appropriate medical insurance premium or reimbursement of an insurance claim relating to treatment of the subject.

In other aspects methods for determining the efficacy of a treatment for glucoregulatory dysfunction are provided wherein the method comprises (a) separating diacylglycerols from a biosample isolated from a subject undergoing treatment for glucoregulatory dysfunction; (b) determining the concentration of one or more diacylglycerol fatty acid species comprising the separated diacylglycerols; and (c) determining the efficacy of the treatment for glucoregulatory dysfunction when the concentration of one or more diacylglycerol fatty acid species is increased or decreased relative to a pre-treatment level or range.

As used herein "pre-treatment level" or "pre-treatment range" refers to the concentration of a biomarker, including but not limited to a component of a blood lipid profile and more specifically a diacylglycerol species in a patient sample collected prior to the patient receiving treatment for glucoregulatory dysfunction. Pre-treatment levels can include an average of multiple measurements of the biomarker or range of biomarker concentrations based on multiple measurements from a patient.

The invention will be further described in the following examples, which do not limit the scope of the invention described in the claims.

The Examples that follow are illustrative of specific embodiments of the invention and various uses thereof. They are set forth for explanatory purposes only and are not to be taken as limiting the invention.

EXAMPLES

Example 1: Methods

Animal Care and Assessments

The experiments described herein involved adult male rhesus monkeys of Indian origin from 10 to 22 years of age. Animals were housed individually at the Wisconsin National Primate Research Center and were allowed ad libitum access to food for 6-8 hours per day. All animals were fed a pelleted, semi-purified diet (Teklad, Madison Wis.), which contained 15% lactabumin, 10% corn oil and approximately 65% carbohydrate in the form of sucrose and cornstarch as previously described (Ramsey et al., 2000, Exp Gerontol 35: 1131-1149). Animals had continuous access to water and rooms were maintained at 21-26° C. with ~50-65% relative humidity. Animals were monitored daily, body weight monitored weekly, and body composition monitored every 6 months by dual energy X-ray absorptiometry (DXA). Glucoregulatory function was monitored every 6 months using established criteria, where levels of fasting plasma glucose and insulin were determined and insulin sensitivity measured using a frequently sampled intravenous glucose tolerance test (FSIGTT) as previously described (Ramsey et al., 2000, J Med Primatol 29: 11-19; Gresl et al., 2001, Am J Physiol Endocrinol Metab 281: E757-765). Plasma samples drawn >3 hrs following glucose infusion during the FSIGTT, a time-point when baseline measures of insulin and glucose are reestablished, were stored at −80° C. for subsequent analysis as outlined below.

The nonhuman primate rhesus macaque (*Macaca mulatta*) is used to illustrate the invention disclosed herein because this species is recognized in the art as being useful for providing insights into human disease biology. Rhesus monkeys share marked anatomical, physiological and behavioral similarities with humans and many diseases and disorders exhibited in humans are also observed in rhesus monkeys (Hudson et al., 1996, Aging (Milano) 8: 197-204; Raman et al., 2005, J Gerontol A Biol Sci Med Sci 60: 1518-1524; Ramsey et al., 2000, J Med Primatol 29: 11-19; Uno, 1997, Age (Omaha) 20: 1-13). In addition, conditions that increase in prevalence with advancing age in humans are also manifest in aging rhesus monkeys; these diseases and disorders include but are not limited to neoplasia, sarcopenia, bone loss, loss of immune function, and diabetes (Uno, 1997, Id.; Austad & Fischer, 2011, ILAR J 52: 78-88; ILAR (U.S.). Committee on Animal Models for Research on Aging, 1981, Mammalian Models for Research on Aging: National Academies 587). Importantly, cross-sectional studies confirm that lipoprotein profiles and plasma triacylglycerol levels track with metabolic disease in rhesus monkeys in the same manner as for human clinical evaluations (Ding et al., 2007, Metabolism 56: 838-846; Kemnitz, 1989, J Clin Endocrinol Metab 69: 287-293).

Eight animals were identified as metabolically impaired when the following criteria were satisfied: fasting insulin greater than 70 microU/ml and insulin sensitivity index (Si) less than 2(E-04) (no units) as determined by frequently sampled intravenous glucose tolerance testing in combination with an irregular glucose response curve (Table 1). The eight control animals were matched to impaired animals for age and weight at time of diagnosis but differed in that they had normal levels of fasting insulin, and Si greater than 2 with normal glucose-response curves. To investigate the trajectory of metabolic dysfunction onset, data and plasma samples were analyzed from both groups of animals at a time two years prior to diagnosis, when all 16 animals were healthy as defined by the above metrics, and then at the time of diagnosis of glucoregulatory impairment in the same animals (FIG. 1A).

Although the healthy controls were matched by weight to metabolically impaired animals at the time of diagnosis, body composition including abdominal circumference and percent body fat were not part of the selection criteria. Median BMI was not significantly different between healthy and metabolically impaired animals at time of these observations or two years prior to diagnosis. Dual energy X-ray absorptiometry (DXA) measures of body composition revealed no significant difference in total body fat, percent fat, abdominal fat (FIG. 1B), or percent abdominal fat (not shown) between groups at both time points. Abdominal circumference (central adiposity) was also not significantly different between groups at either time point. Each of these measures increased with age for both groups but the difference was not significant.

TABLE 1

Study Cohort

| | At time of diagnosis | | | | |
|---|---|---|---|---|---|
| | Age (y) | Wt (Kg) | Glucose mg/dl | Insulin microU/ml | Si (E−04)* |
| Healthy | 16.82 ± 1.6 | 14.41 ± 1.6 | 62.63 ± 2.57 | 42.38 ± 7.55 | 3.46 ± 1.09 |
| Impaired | 17.68 ± 1.74 | 14.76 ± 1.18 | 85.06 ± 13.45 | 146.41 ± 33.27 | 0.54 ± 0.12 |

| | Two years prior to diagnosis | | | | |
|---|---|---|---|---|---|
| | Age (y) | Wt (Kg) | Glucose | Insulin | Si (E−04)* |
| Healthy | 14.83 ± 1.6 | 13.77 ± 0.86 | 59.63 ± 2.01 | 32.88 ± 1.09 | 3.61 ± 1.09 |
| Pre-Impaired | 15.68 ± 1.73 | 13.96 ± 1.01 | 65.16 ± 3.09 | 48.78 ± 6.72 | 2.53 ± 0.89 |

Shown in this table are biometric data presented as means±SEM (n=8 per group), wherein the values in bold are significantly different (p<0.05), wherein insulin sensitivity (Si (E−04)*) was generated by the modified minimal model approach utilizing data from the intravenous frequently sampled glucose tolerance test.

Adipose tissue distribution and signaling becomes deregulated with age (Clement & Langin, 2007, J Intern Med 262: 422-430; Das et al., 2004, Obes Rev 5: 13-19; Kirkland et al., 2002, Exp Gerontol 37: 757-767) and age increases the risk of metabolic disease, providing a suggestion that disrupted adipose tissues have a function in disease vulnerability. In this example, adiposity, abdominal circumference, and percent abdominal adiposity were not significantly different between healthy and impaired animals at time of diagnosis or two years earlier comparing the animals that remained healthy and those that went on to develop metabolic syndrome. Reduced adiponectin production from adipose tissue is a possible distinction for disease risk as shown Table 2 (Model 4). Adiponectin is a peptide hormone secreted from adipose tissue that enhances lipid utilization in target tissues, wherein lower circulating levels are predicted to negatively impact peripheral tissue lipid metabolism. Data shown here are consistent with adiponectin playing a role in metabolic syndrome development. These data also are consistent with adipose tissue dysfunction rather than adiposity per se as being a contributing factor in metabolic disease progression. Accordingly, provided herein is experimental evidence from a recognized animal model of human disease suggesting that metabolic disease risk is due to differences in underlying lipid metabolism.

Statistical Approach

Three sets of variables are analyzed: those measured two years before diagnosis, at diagnosis and any change between the two. The relationship between each measured variable and impairment status was evaluated using logistic regression. Odds ratios that summarized the change in odds of impairment for a one standard deviation change in the variable are provided herein. The relationship among the measured variables is summarized using rank based (Spearman) correlations. The ability of the groups of measured variables to jointly predict impairment status was assessed using lasso logistic regression fit with cross-validation. P-values are reported without adjustment and should be interpreted as a measure of the amount of evidence in the data for the relationship being tested. The R statistical analysis package was used for all analysis and specifically the package glmnet (Friedman et al., 2010, J Stat Softw 33: 1-22).

Example 2: Fatty Acid Composition Analysis

Total lipids from experimental animals as described in Example 1 were extracted from ~200 μl of fasting plasma according to the method of Bligh and Dyer (1959, Can J Biochem Physiol 37: 911-917), and separated by silica gel thin layer chromatography using a mixture of petroleum ether:diethyl ether:acetic acid (at a ratio of 80:30:1) as the developing solvent. Lipids derived from trigylcerides, phospholipids, free fatty acids and diacylglycerol were scraped, methylated, and analyzed by gas-liquid chromatography on a capillary column coated with DB-225 (30-m length, 0.25 mm, internal diameter, 0.25 μm; Agilent Technologies, Inc., Wilmington, Del.). Fatty acids were identified by comparison of retention times with authentic standards (Sigma). Pentadecanoic acid (15:0) was included as an internal standard to control for transmethylation efficiency. Except for absolute concentrations of DAG and FFA (where n=5 control and n=7 impaired), all analyses including relative levels of DAG and FFA were conducted on n=8 control and n=8 impaired for each time point.

Figure 2:
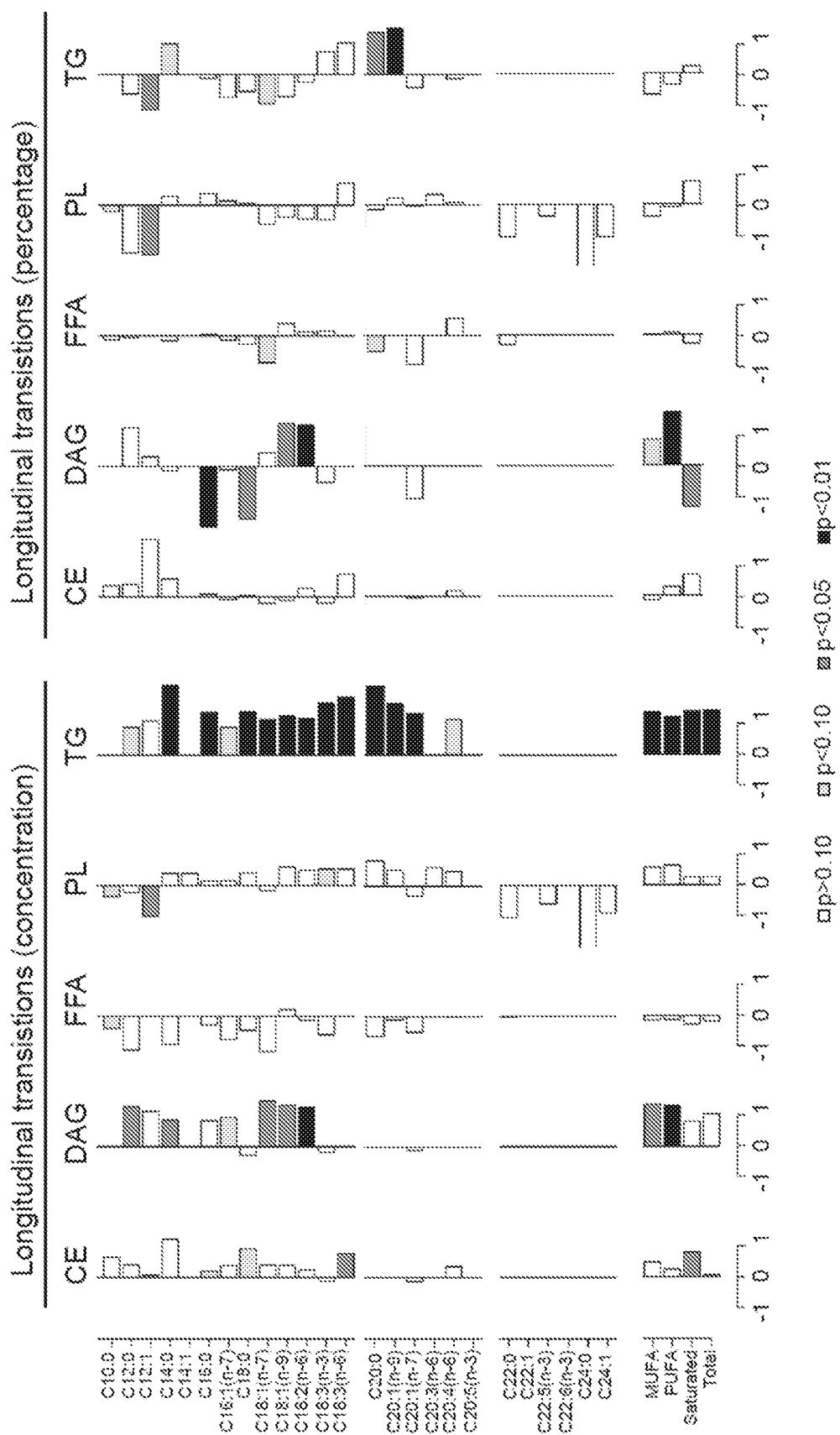
FIG. 2 illustrates longitudinal changes in plasma fatty acid profiles with progression toward metabolic syndrome in rhesus monkeys. Data are shown as differences in the change in median values from two years prior to diagnosis to time of diagnosis between metabolic impaired and control animals with units shown as median difference adjusted for the median absolute deviation of each variable measured for fatty acid species in plasma cholesterol ester (CE), diacylglycerol (DAG), free fatty acid (FFA), phospholipid (PL), and triacylglycerol (TG) lipid classes. Left: actual levels. Right: relative abundance expressed as a percentage of total species detected within class.
Figure 3:
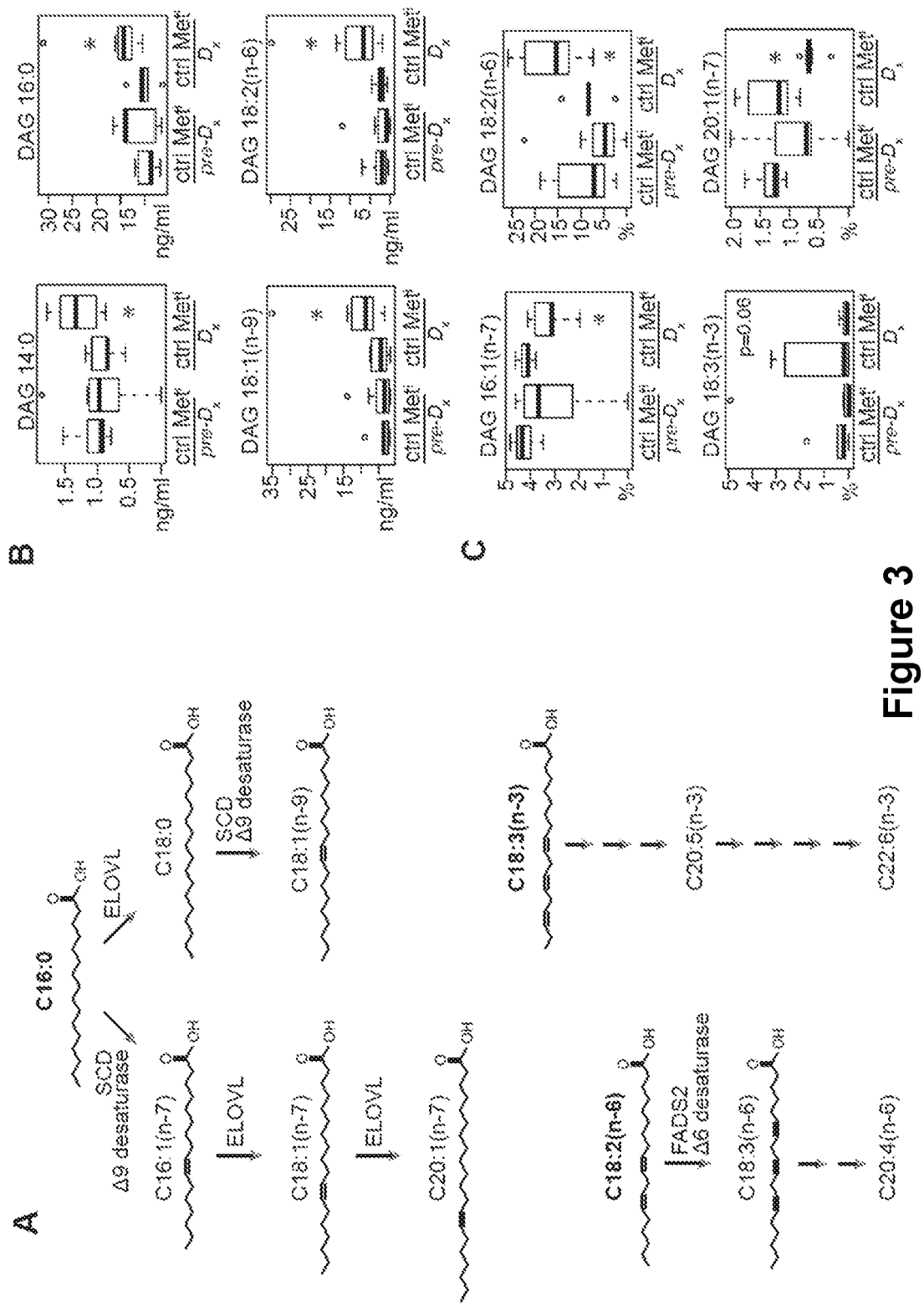
FIGS. 3A-3C illustrate observed changes in plasma diacylglycerol (DAG) fatty acids with progression to metabolic syndrome in rhesus monkeys.
Figure 7:
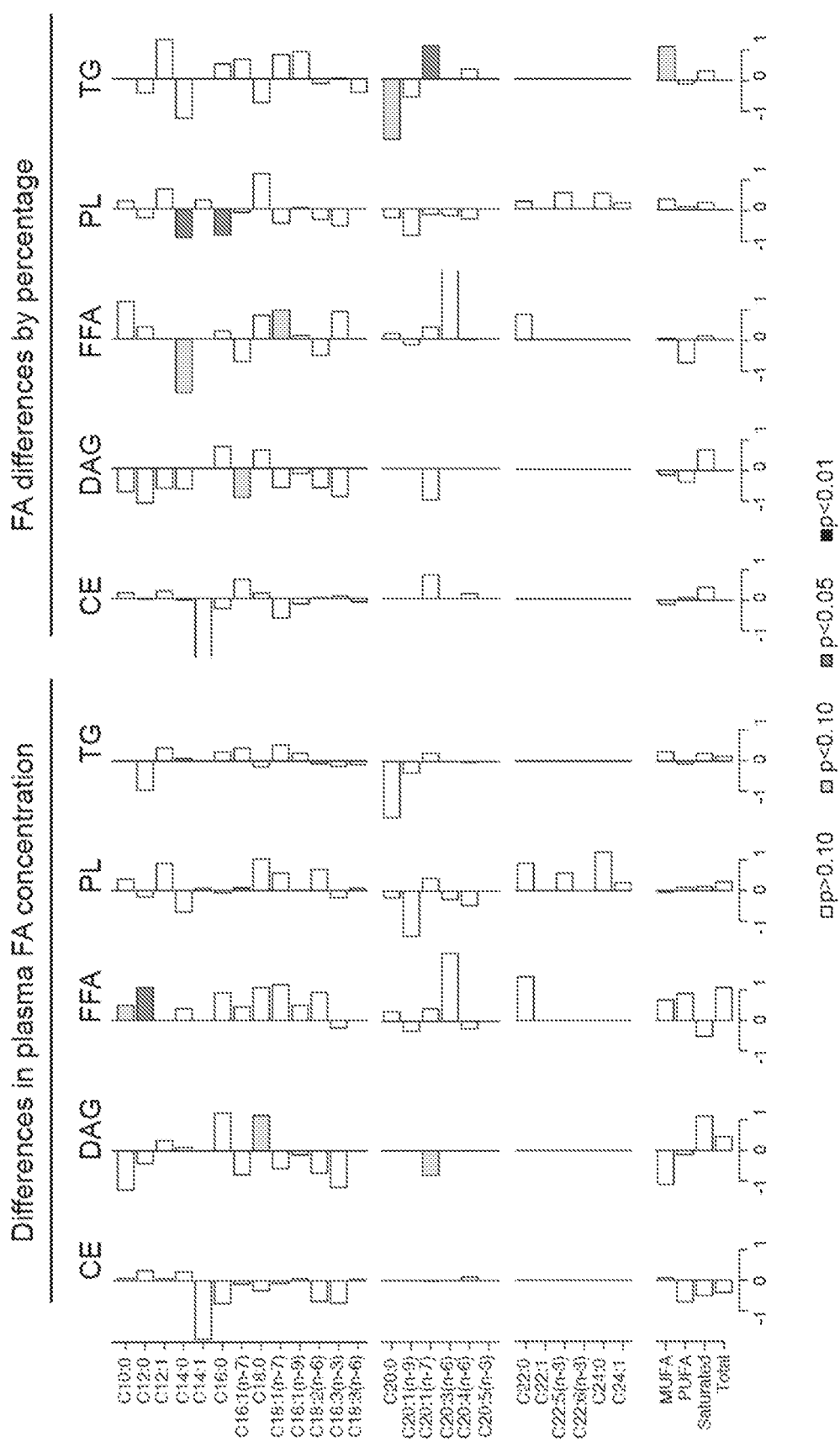
FIG. 7 illustrates plasma fatty acid profiles in healthy and pre-impaired animals two years prior to diagnosis. Data are shown as the difference in median values between metabolic-impaired and control animals with units adjusted for the median absolute deviation of each variable measured for indicated fatty acid species in plasma: cholesterol ester (CE), diacyglycerol (DAG), free fatty acid (FFA), phospholipid (PL), and triacylglycerol (TG) lipid classes. Left: actual levels. Right: relative abundance expressed as a percentage of total species detected within class.
Figure 8:
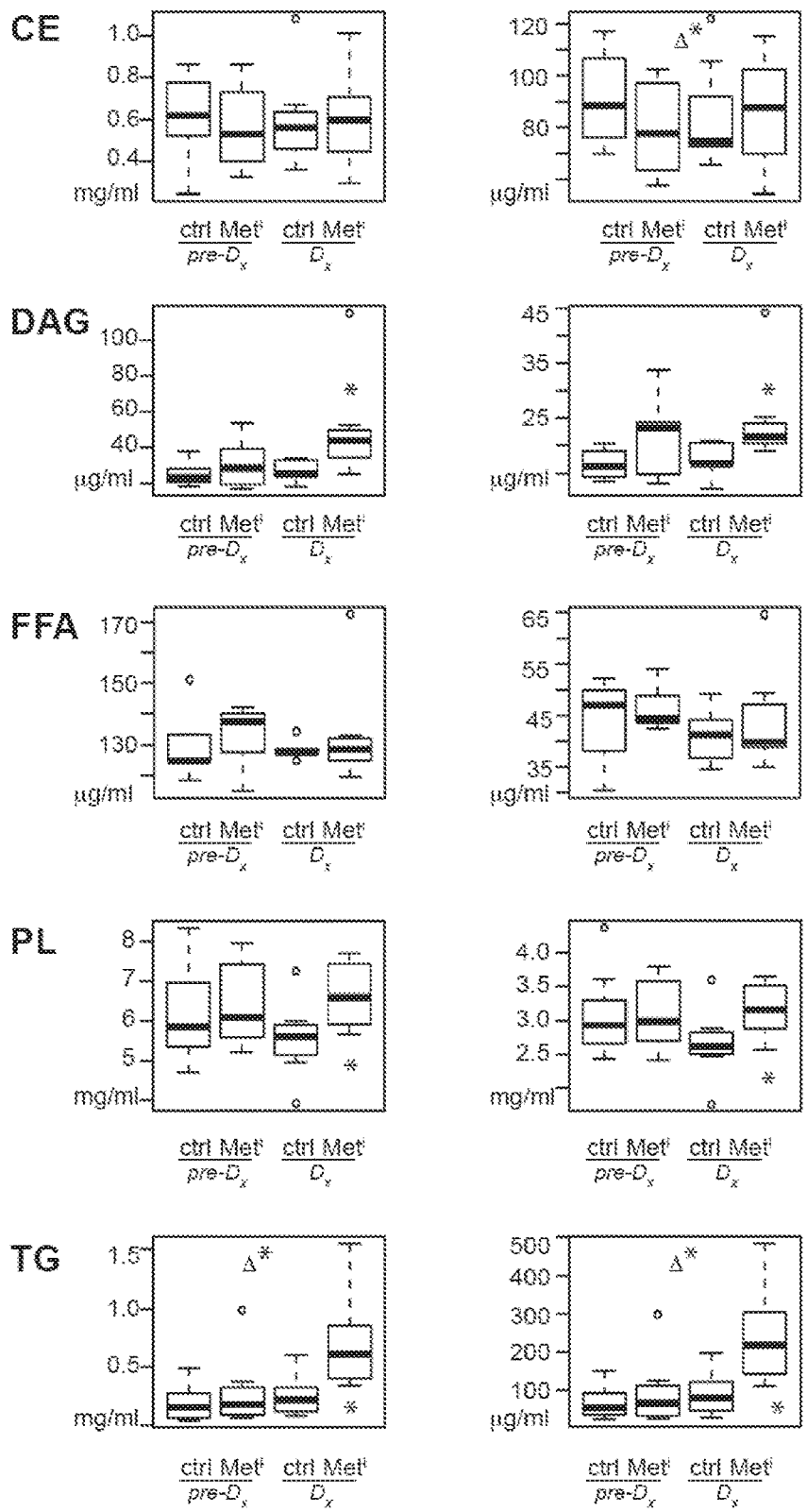
FIG. 8 are graphs illustrating metabolic syndrome progression and changes in plasma total and saturated fatty acids. Differences in median actual levels of indicated fatty acid species in plasma cholesterol ester (CE), diacylglycerol (DAG), free fatty acid (FFA), phospholipid (PL), and triacylglycerol (TG) lipid classes separated by TLC and detected using GC. Data are shown as medians and IQR in metabolic impaired (Meti) and age- and weight-matched controls (Ctrl) at time of diagnosis (Dx) and two years prior to diagnosis (pre-Dx). *$p<0.05$ control vs impaired, Δ*p value<0.05 for difference between the changes for impaired and control animals from two years prior to time of diagnosis.
Figure 9:
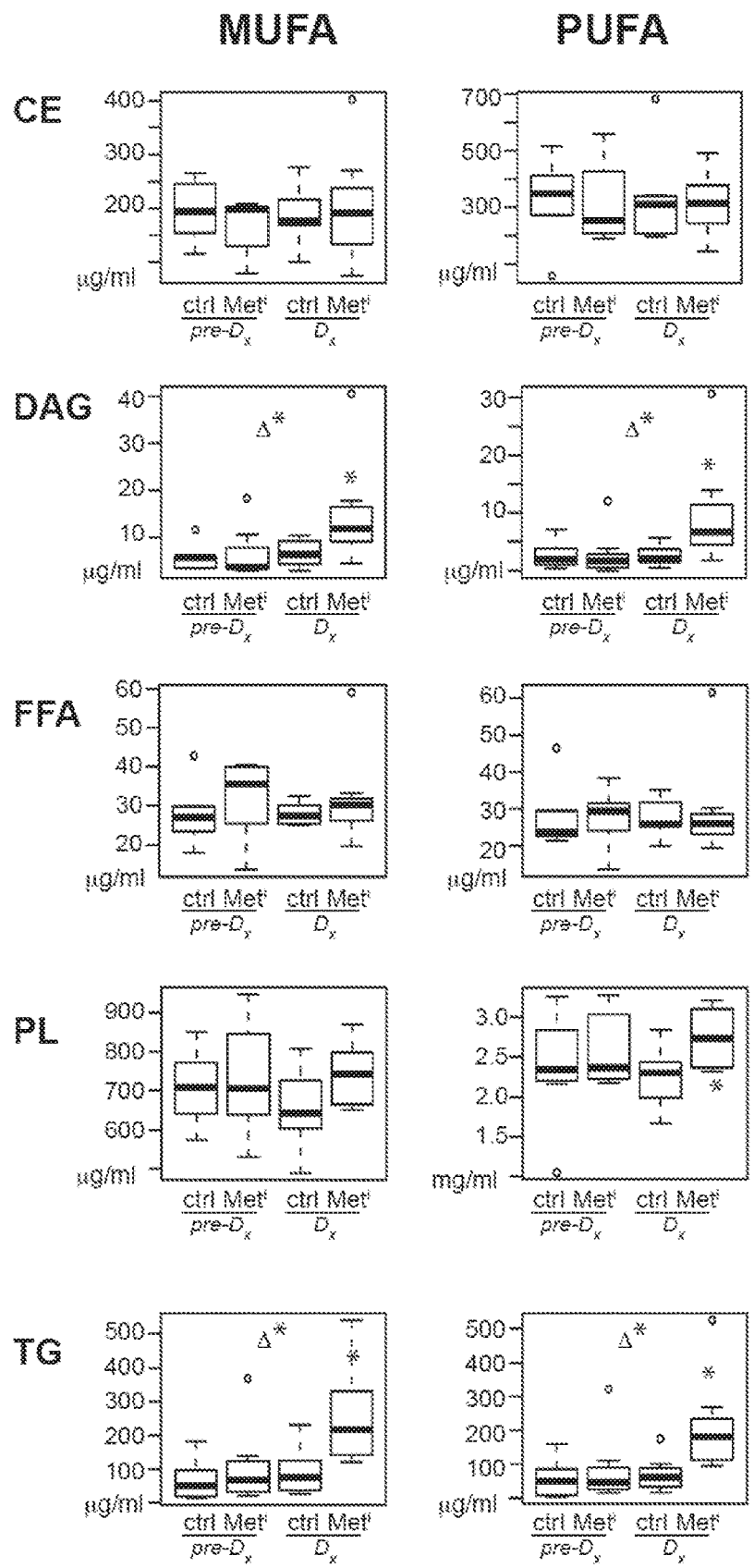
FIG. 9 are graphs illustrating metabolic syndrome progression and changes in plasma MUFA and PUFA. Differences in median actual levels of indicated fatty acid species in plasma cholesterol ester (CE), diacylglycerol (DAG), free fatty acid (FFA), phospholipid (PL), and triacylglycerol (TG) lipid classes separated by TLC and detected using GC are shown. Data are shown as medians and IQR in metabolic impaired (Meti) and age and weight matched controls (Ctrl) at time of diagnosis (Dx) and two years prior to diagnosis (pre-Dx). *$p<0.05$ control vs impaired, Δ*p value<0.05 for difference between the changes for impaired and control animals from two years prior to time of diagnosis.
Figure 10:
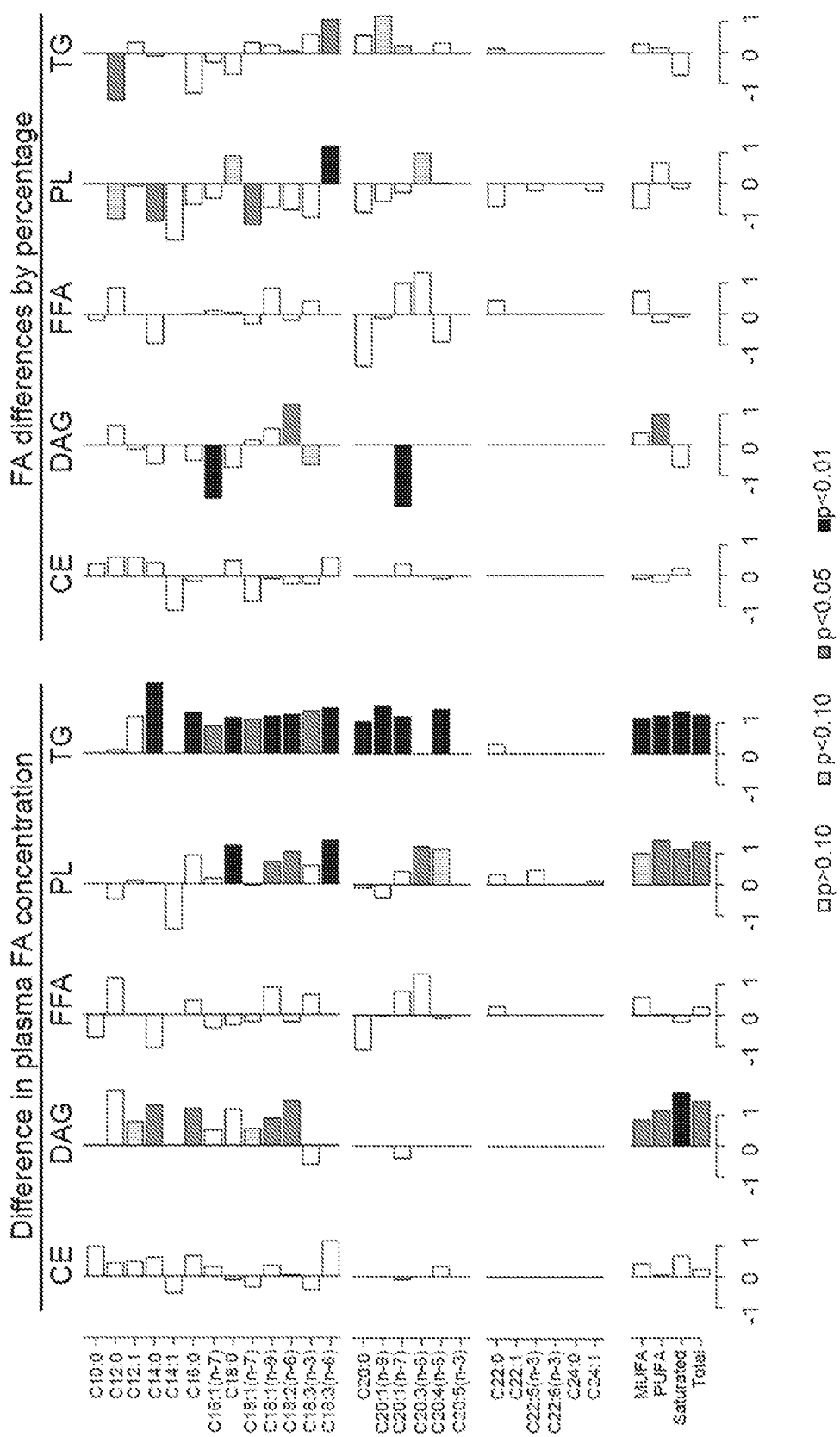
FIG. 10 illustrates distinct plasma fatty acid profiles in metabolic-impaired animals at time of diagnosis. Data are shown as the difference in medians between metabolic-impaired and control with units adjusted for the median absolute deviation of each variable measured for indicated fatty acid species in plasma cholesterol ester (CE), diacylglycerol (DAG), free fatty acid (FFA), phospholipid (PL), and triacylglycerol (TG) lipid classes. Left: actual levels. Right: relative abundance expressed as a percentage of total species detected within class.

Fatty acid composition of CE, FFA, DAG, PL, and TG was determined using gas chromatography. Using this technique, fatty acids of up to 24 carbon units were detected, and chain length and degree of saturation were resolved including MUFA and PUFA. Two years prior to diagnosis significant differences were observed in DAG and FFA lipid classes only, although differences in composition within class were detected for all but CE (FIG. 9). At the time of diagnosis there were significant increases in plasma total, saturated, MUFA and PUFA levels of fatty acids within DAG, PL and TG classes but not for CE and FFA (shown in FIGS. 7 and 8) from metabolic impaired animals compared to age and weight matched healthy controls; substantial differences in fatty acid composition expressed as a percentage of total of each of these lipid moieties were also detected (FIG. 10). The most striking differences were observed among the TGs, with total TG increased in impaired animals (odds ratio (OR) 31.37, p value<0.001) at time of diagnosis. These data were consistent with metabolic impaired animals being classified as having developed metabolic syndrome according to the following criteria: insulin resistance, plasma TG greater than 80 mg/dl, and adiposity in excess of 25%. In humans, elevation of serum TG has been shown to be tightly associated with metabolic syndrome and correlate with accumulation of visceral fat (Taksali et al., 2008, Diabetes 57: 367-371; Wisse, 2004, J Am Soc Nephrol 15: 2792-2800). Longitudinal data were analyzed to identify differences in the trajectory of change over the two-year period during which one half of the animals remained healthy and the other half transitioned to metabolic syndrome (FIG. 2). Selective increases in specific fatty acid species resulted in a difference in the overall percent concentration in lipid classes in impaired animals compared to controls. These data suggested that pathways of fatty acid elongation and desaturation are differentially regulated in impaired animals (FIG. 3A) compared with normal control animals. Significant differences detected in these comparisons included changes in circulating DAG concentrations for discrete species in the C12 to C18 ranges (FIG. 3B). Lasso logistical analysis revealed that changes in DAG C18:2(n-6) alone could predict disease status (OR 39.23, p value<0.001) with 92% success. Lasso logistical analysis identified a model that predicted metabolic impairment 100% correctly (Table 2-Model 1) based on FA composition of DAG at time of diagnosis (Table 2, FIG. 3C). Recent reports have shown that intracellular DAG influences the rate of de novo lipogenesis and can negatively impact insulin sensitivity in a tissue specific manner (Samuel & Shulman, 2012, Cell 148: 852-871, although it is currently unclear whether circulating DAG have signaling capabilities.

TABLE 2

Predictive Models for Insulin Resistance

Model 1 DAG percent concentration at diagnosis

| Fatty acid | OR* | SD | Prediction |
|---|---|---|---|
| C16:1 | −61.4 | 0.569 | 100% |
| C18:2(n-6) | 169.4 | 5.274 | |
| C18:3(n-3) | −9.7 | 0.181 | |
| C20:1(13-cis) | −35.8 | 0.19 | |
| Moiety | OR* | SD | Prediction |

Model 2 Lipoprotein profile pre-diagnosis

TABLE 2-continued

Predictive Models for Insulin Resistance

| HDL total | −31.1 | 8.154 | 88% |
|---|---|---|---|
| HDL large particles | −13.2 | 2.817 | |
| IDL | −7.5 | 30.393 | |
| HDL cholesterol | −23.9 | 5.189 | |

Model 3 Lipoprotein profile at diagnosis

| HDL total | −88.1 | 11.12 | 100% |
|---|---|---|---|
| HDL small particles | −100 | 2.15 | |
| IDL | 918.6 | 29.652 | |
| Triacylglycerols | 7116.8 | 80.06 | |

Model 4 Lipid metabolism index

| PL C18:0 | 65.2 | 237.8 | 100% |
|---|---|---|---|
| PL C18:3(n-6) | 21.4 | 2.5 | |
| TG C14:0 | 1.0 | 3.4 | |
| HDL total | −43.3 | 4.4 | |
| HDL large particles | −13.5 | 1.9 | |
| LDL large particles | 15.8 | 126.0 | |
| Triacylglycerols | 42.3 | 80.1 | |
| Adiponectin HMW | −1.3 | 128.5 | |

*OR: odds ratio for change in 1 SD

Figure 4:
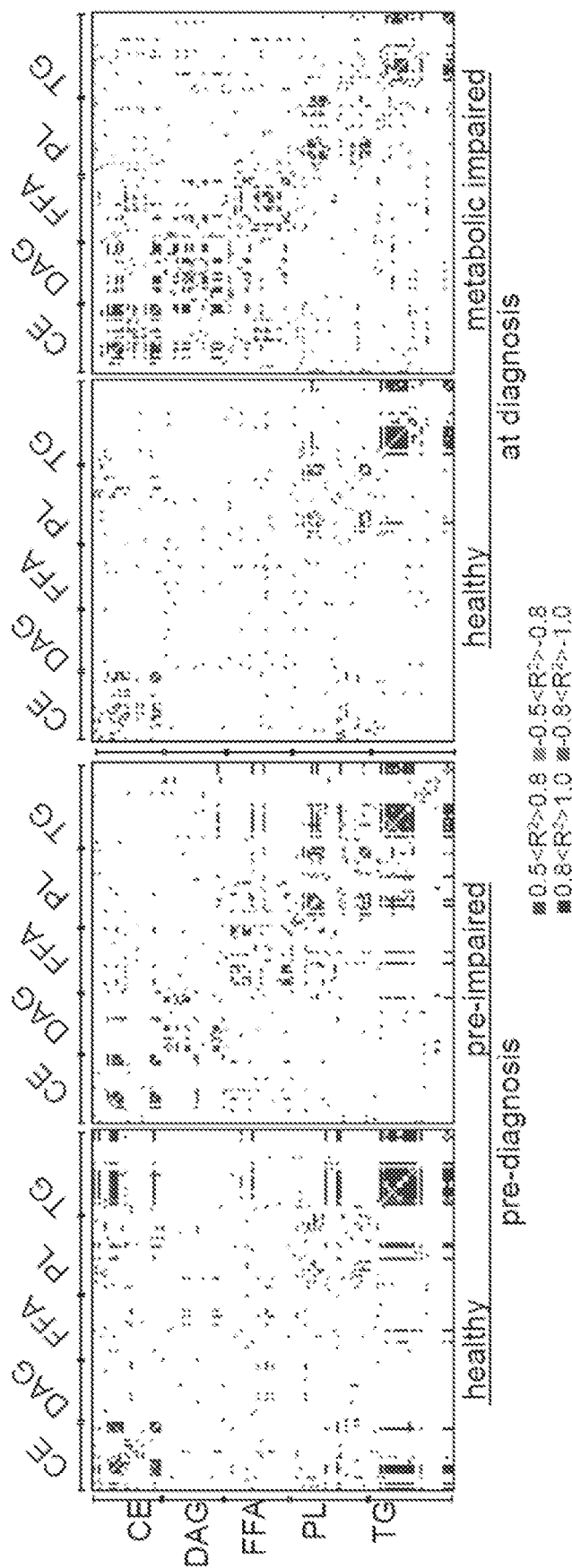
FIG. 4 shows statistical correlations demonstrating that metabolic syndrome was associated with plasma fatty acids within and among lipid classes in rhesus monkeys. Correlations for plasma concentrations of fatty acids from plasma cholesterol ester (CE), diacylglycerol (DAG), free fatty acid (FFA), phospholipid (PL), and triacylglycerol (TG) lipid classes for healthy and impaired animals at time of diagnosis and two years prior (when all animals were clinically identified as healthy). Significant positive and negative correlations are shown for the following fatty acids in each class top to bottom and left to right in this order: C10:0, C12:0, C12:1, C14:0, C14:1, C16:0, C16:1, C18:0, C18:1 (n-9), C18:1(n-7), C18:2(n-6), C18:3(n-6), C18:3(n-3), C20:0, C20:1(n-9), C20:1(n-7), C20:3(n-6), C20:4(n-6), C22:0, C22:5(n-3), saturated, monounsaturated fatty acids (MUFA), polyunsaturated fatty acids (PUFA), total fatty acids.
Figure 11:
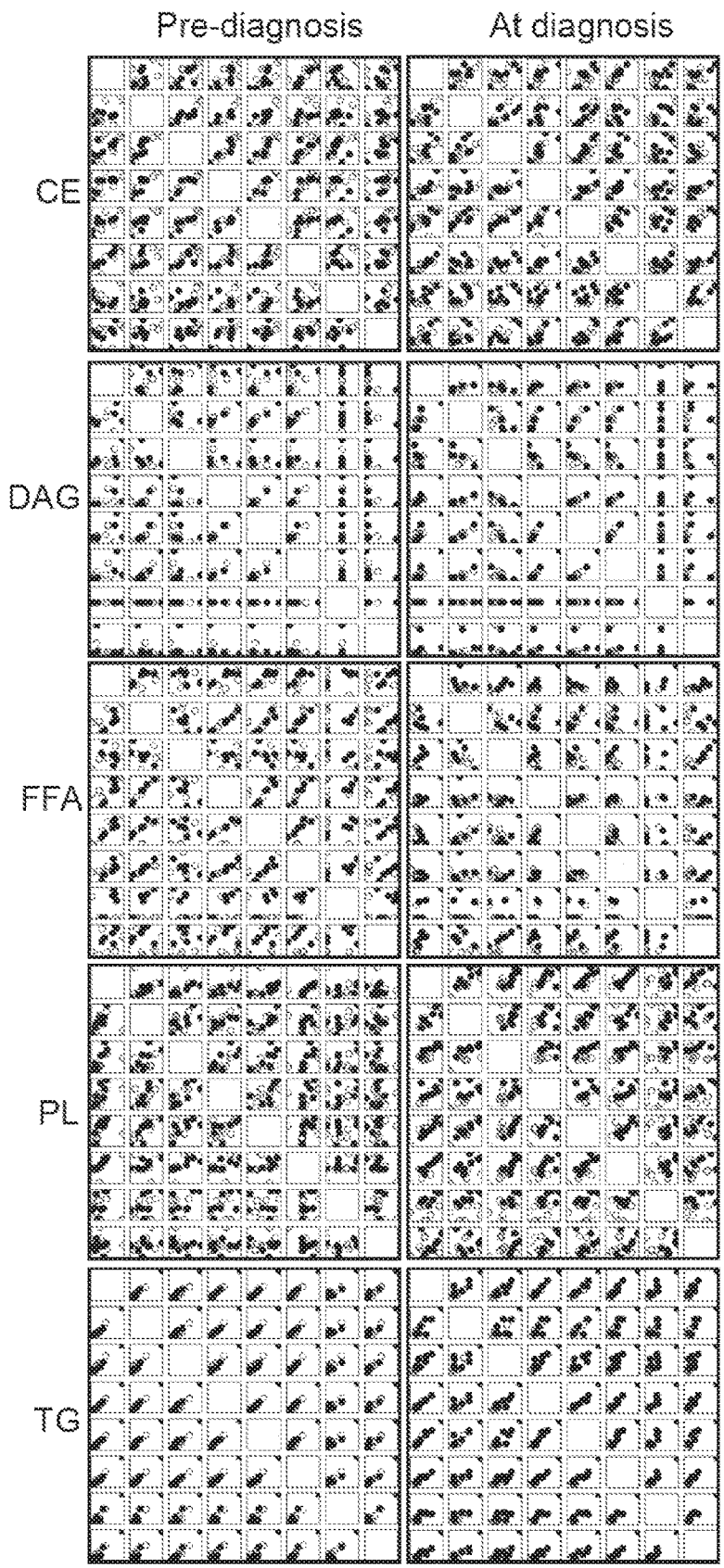
FIG. 11 illustrates lipid class-specific fatty acid correlations between healthy and impaired animals two years prior to and at time of diagnosis. Correlations shown are for C16 and C18 chain length fatty acids from plasma cholesterol ester (CE), diacylglycerol (DAG), free fatty acid (FFA), phospholipid (PL), and triacylglycerol (TG) lipid classes for healthy and impaired animals at time of diagnosis (right panels) and two years prior (left panels) when all animals were clinically identified as healthy. Data are shown as plasma concentration for control (open circles) and (pre-)impaired animals (closed circles) for the following fatty acids in each class top to bottom and left to right in this order: C16:0, C16:1, C18:0, C18:1 (n-9), C18:1 (n-7), C18:2 (n-6), C18:3 (n-6), C18:3 (n-3). Scales are not equivalent.
Figure 13:
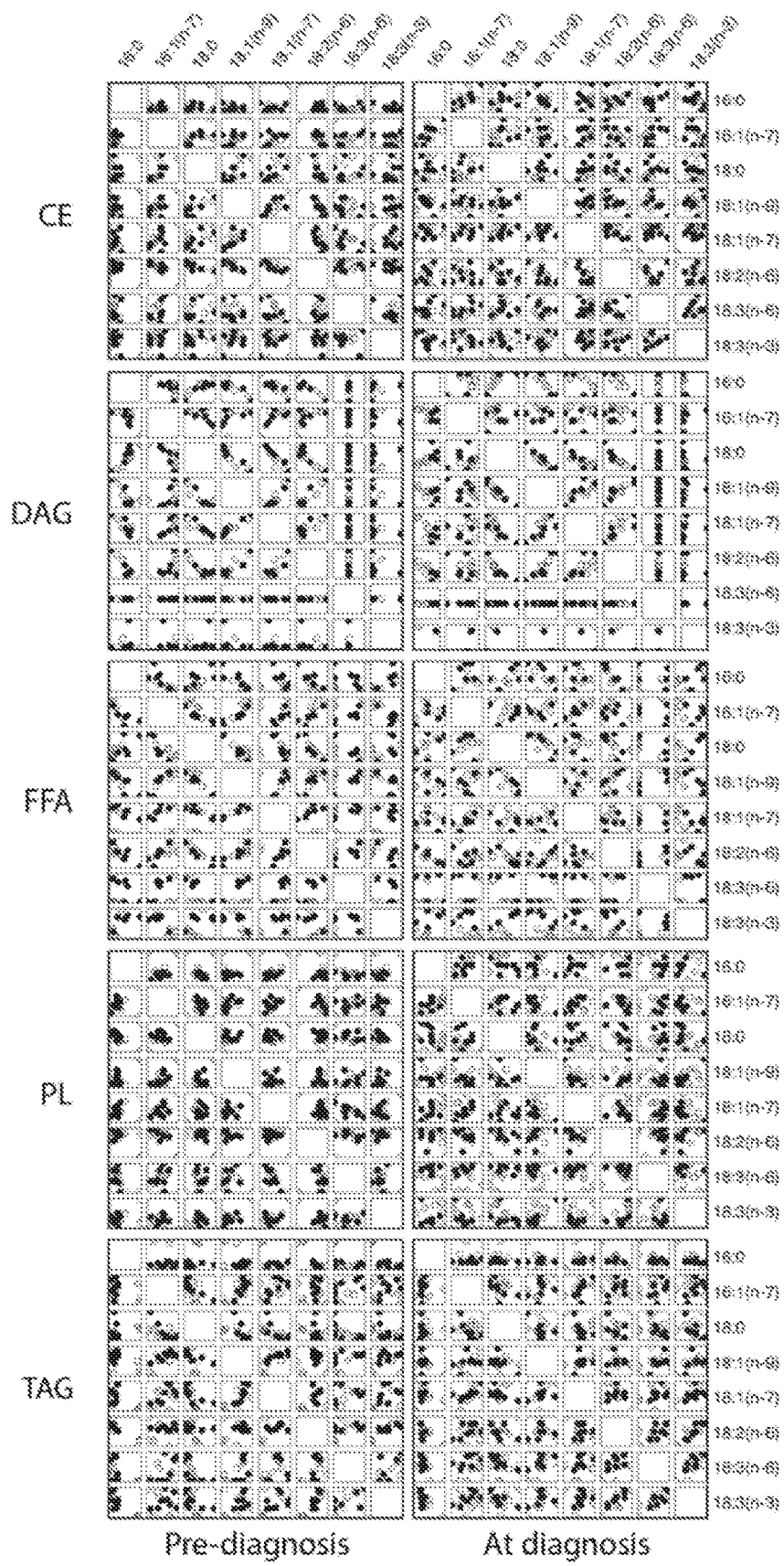
FIG. 13 illustrates lipid class-specific fatty acid correlations between healthy and impaired animals two years prior to and at time of diagnosis. Correlations shown are for C16 and C18 chain length fatty acids from plasma cholesterol ester (CE), diacylglycerol (DAG), free fatty acid (FFA), phospholipid (PL), and triacylglycerol (TG) lipid classes for healthy and impaired animals at time of diagnosis (right panels) and two years prior (left panels) when all animals were clinically identified as healthy. Data are shown as plasma percent concentration for control (open circles) and (pre-)impaired animals (closed circles) for the following fatty acids in each class top to bottom and left to right in this order: C16:0, C16:1, C18:0, C18:1 (n-9), C18:1 (n-7), C18:2 (n-6), C18:3 (n-6), C18:3 (n-3). Scales are not equivalent.
Figure 14:
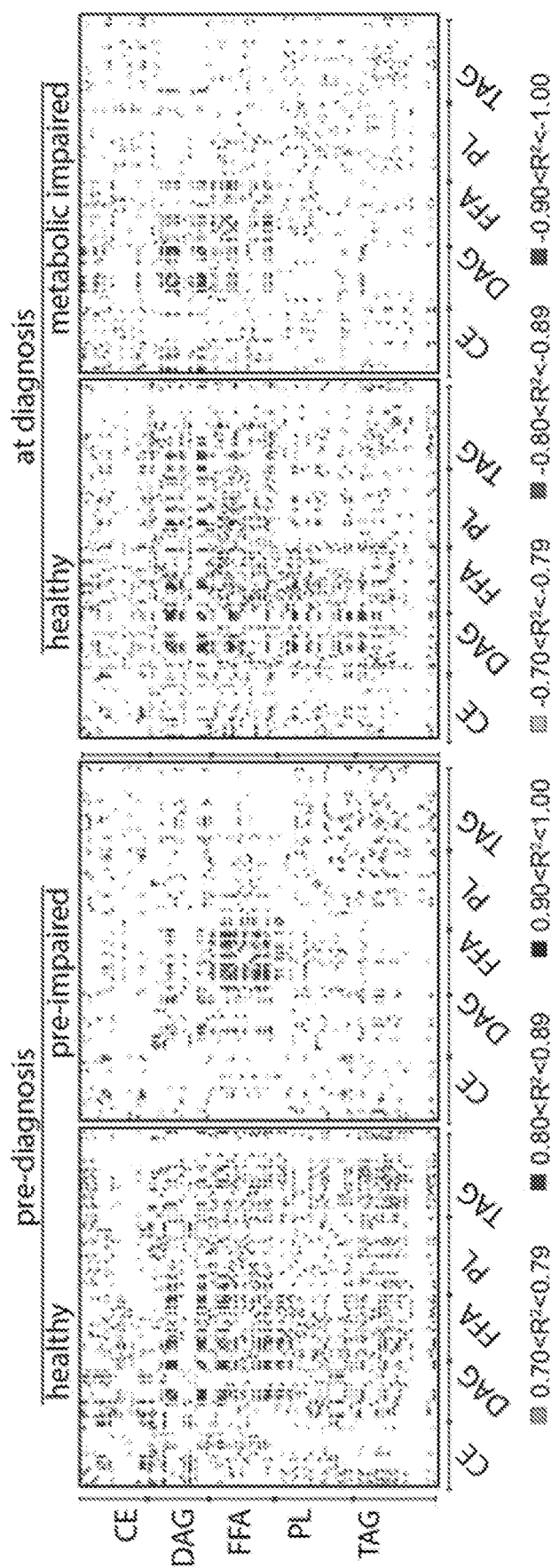
FIG. 14 shows statistical correlations demonstrating that metabolic syndrome was associated with plasma fatty acids within and among lipid classes in rhesus monkeys. Correlations for percent concentration of fatty acids from plasma cholesterol ester (CE), diacylglycerol (DAG), free fatty acid (FFA), phospholipid (PL), and triacylglycerol (TG) lipid classes for healthy and impaired animals at time of diagnosis and two years prior (when all animals were clinically identified as healthy). Significant positive and negative correlations are shown for the following fatty acids in each class top to bottom and left to right in this order: C10:0, C12:0, C12:1, C14:0, C14:1, C16:0, C16:1, C18:0, C18:1 (n-9), C18:1(n-7), C18:2(n-6), C18:3(n-6), C18:3(n-3), C20:0, C20:1(n-9), C20:1(n-7), C20:3(n-6), C20:4(n-6), C22:0, C22:5(n-3), saturated, monounsaturated fatty acids (MUFA), polyunsaturated fatty acids (PUFA), total fatty acids.
Figure 15:
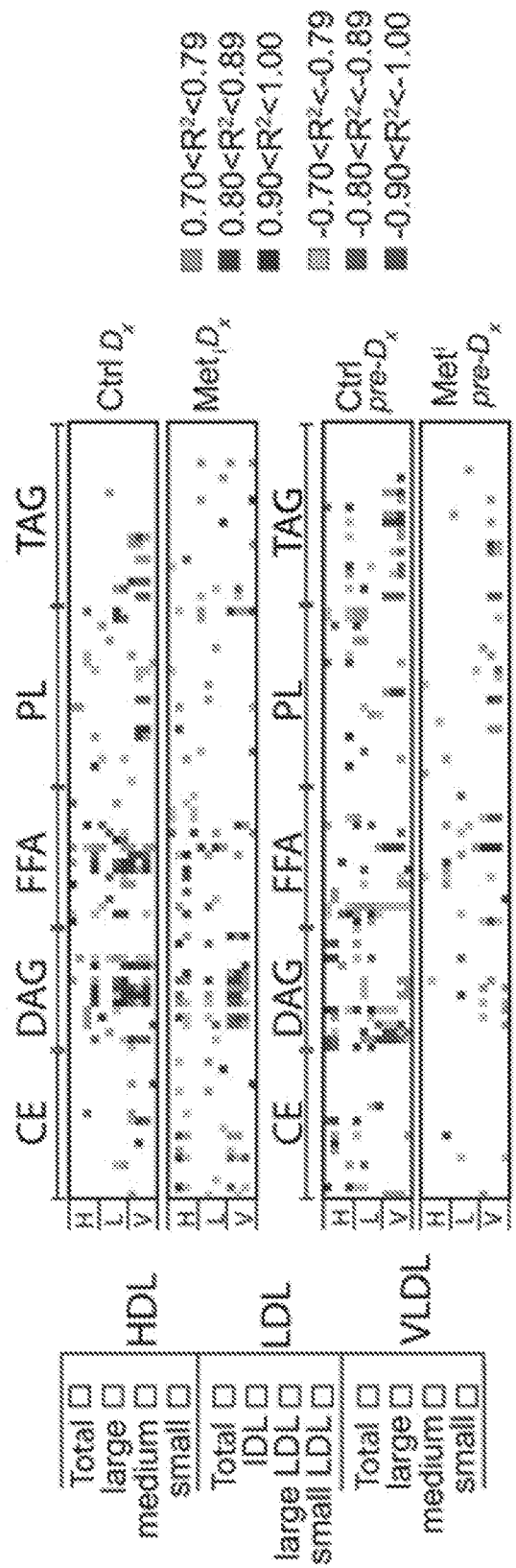
FIG. 15 illustrates positive and negative correlations for the indicated plasma lipoproteins and associated metrics with percent concentration of the following fatty acids in each class top to bottom and left to right in this order: C10:0, C12:0, C12:1, C14:0, C14:1, C16:0, C16:1, C18:0, C18:1 (n-9), C18:1(n-7), C18:2(n-6), C18:3(n-6), C18:3(n-3), C20:0, C20:1(n-9), C20:1(n-7), C20:3(n-6), C20:4(n-6), C22:0, C22:5(n-3), saturated, MUFA, PUFA, total fatty acids. *$p<0.05$ control vs impaired, Δ*p value<0.05 for difference between the changes for impaired and control animals from two years prior to time of diagnosis.

To determine relationships among fatty acid species within and among lipid classes, Spearman rank correlations among the fatty acid for each group at each time point were calculated based on plasma concentration (FIG. 4). Strong positive and negative (absolute $R^2 \geq 0.7$) correlations were differentially detected based on glucoregulatory status. Overt differences in correlations within and among lipid classes were observed for metabolic impaired animals at time of diagnosis compared to age- and weight-matched healthy controls and compared to themselves at the earlier time point. Specifically, strong correlations were detected within DAG that were unique to the metabolic impaired animals and also correlated with species within CE and FFA. Spearman rank correlations among fatty acids based on percent concentration were also calculated (FIG. 14). In healthy animals at both time points strong correlations were detected broadly among lipid classes suggesting a high degree of connectivity in fatty acid composition. In contrast, in pre-impaired animals strong correlations were clustered among fatty acids within FFA, at time of diagnosis strong correlations were detected among DAG and FFA, and at both time points fewer strong correlations among other lipid classes were detected in (pre-)impaired animals compared to healthy controls. These data suggest that differences in lipid metabolism in metabolic syndrome animals extend beyond the established clinical diagnostic of an increase in circulating levels of TG and that changes may be occurring earlier than previously appreciated. To further delineate divergence in lipid parameters in the transition to disease onset, correlations between groups at both time points were compared based on plasma concentration (FIG. 11), or percent concentration (FIG. 13). Data were plotted for C16 to C18 fatty acids against each other for each lipid class using pooled data from healthy and pre-impaired animals at each time point, i.e. two years prior to diagnosis when all animals were insulin sensitive (left) and the same animals at time of diagnosis when the impaired animals were insulin resistant (right) Spearman rank correlations among fatty acids of C16 to C18 were specific to lipid class and not equivalent among classes for both plasma concentration (Table 3) and plasma percent concentration (Table 4). These data suggested that there are overt differences in lipid metabolism in metabolic syndrome animals at the time of diagnosis, and several of these changes are manifest in advance of clinical indicators of glucoregulatory impairment.

TABLE 3

Spearman rank correlations greater than 0.7 among C16 and C18 fatty acids by lipid class based on plasma concentration

| | Pre-diagnosis (n = 16, 12, 12, 16, 16) | | | | | | | |
|---|---|---|---|---|---|---|---|---|
| Fatty acid | 16:0 | 16:1(n-7) | 18:0 | 18:1(n-9) | 18:1(n-7) | 18:2(n-6) | 18:3(n-6) | 18:3(n-3) |
| CE. 16:0 | | | | 0.73 | | 0.88 | | |
| CE. 16:1(n-7) | | | 0.84 | 0.83 | 0.81 | | | |
| CE. 18:0 | | 0.84 | | 0.9 | 0.86 | | | |
| CE. 18:1(n-9) | 0.73 | 0.83 | 0.9 | | 0.92 | 0.8 | | |
| CE. 18:1(n-7) | | 0.81 | 0.86 | 0.92 | | 0.76 | | |
| CE. 18:2(n-6) | 0.88 | | | 0.8 | 0.76 | | | |
| CE. 18:3(n-6) | 0.7 | | | | | | | |
| CE. 18:3(n-3) | 0.73 | 0.83 | 0.7 | | | | | |
| DAG. 16:0 | | | | 0.71 | | | | |
| DAG. 16:1 | | | | 0.71 | 0.91 | 0.85 | | |
| DAG. 18:0 | | | | | | | | |
| DAG. 18:1(n-9) | 0.71 | 0.71 | | | 0.79 | 0.85 | | |
| DAG. 18:1(n-7) | | 0.91 | | 0.79 | | 0.94 | | |
| DAG. 18:2(n-6) | | 0.85 | | 0.85 | 0.94 | | | |
| DAG. 18:3(n-6) | | | | | | | | |
| DAG. 18:3(n-3) | | | | | | | | |
| FA. 16:0 | | | | 0.7 | 0.84 | 0.75 | | |
| FA. 16:1(n-7) | | | | 0.99 | 0.79 | 0.95 | | |
| FA. 18:0 | | | | | | | | |
| FA. 18:1(n-9) | 0.7 | 0.99 | | | 0.81 | 0.98 | | |
| FA. 18:1(n-7) | 0.84 | 0.79 | | 0.81 | | 0.81 | | |
| FA. 18:2(n-6) | 0.75 | 0.95 | | 0.98 | 0.81 | | | |
| FA. 18:3(n-6) | | | | | | | | |
| FA. 18:3(n-3) | | | | | | | | |
| PL. 16:0 | | | 0.82 | 0.73 | 0.73 | 0.77 | | |
| PL. 16:1(n-7) | | | | | 0.81 | | | |
| PL. 18:0 | 0.82 | | | 0.72 | 0.76 | 0.84 | | |
| PL. 18:1(n-9) | 0.73 | | 0.72 | | | | | |
| PL. 18:1(n-7) | 0.73 | 0.81 | 0.76 | | | | | |
| PL. 18:2(n-6) | 0.77 | | 0.84 | | | | | |
| PL. 18:3(n-6) | | | | | | | | |
| PL. 18:3(n-3) | | | | | | | | |
| TG. 16:0 | | 0.96 | 0.84 | 0.95 | 0.96 | 0.93 | 0.88 | 0.9 |
| TG. 16:1(n-7) | 0.96 | | 0.88 | 0.99 | 0.99 | 0.96 | 0.9 | 0.93 |
| TG. 18:0 | 0.84 | 0.88 | | 0.9 | 0.91 | 0.96 | 0.88 | 0.94 |
| TG. 18:1(n-9) | 0.95 | 0.99 | 0.9 | | 0.99 | 0.96 | 0.9 | 0.93 |
| TG. 18:1(n-7) | 0.96 | 0.99 | 0.91 | 0.99 | | 0.97 | 0.88 | 0.95 |
| TG. 18:2(n-6) | 0.93 | 0.96 | 0.96 | 0.96 | 0.97 | | 0.91 | 0.98 |
| TG. 18:3(n-6) | 0.88 | 0.9 | 0.88 | 0.9 | 0.88 | 0.91 | | 0.86 |
| TG. 18:3(n-3) | 0.9 | 0.93 | 0.94 | 0.93 | 0.95 | 0.98 | 0.86 | |

| | At diagnosis (n = 16, 12, 12, 16, 16) | | | | | | | |
|---|---|---|---|---|---|---|---|---|
| Fatty acid | 16:0 | 16:1(n-7) | 18:0 | 18:1(n-9) | 18:1(n-7) | 18:2(n-6) | 18:3(n-6) | 18:3(n-3) |
| CE. 16:0 | | | 0.72 | 0.8 | | 0.91 | | |
| CE. 16:1(n-7) | | | 0.79 | | 0.82 | | | |
| CE. 18:0 | 0.72 | 0.79 | | 0.77 | 0.81 | | | |
| CE. 18:1(n-9) | 0.8 | | 0.77 | | 0.77 | 0.86 | | 0.73 |
| CE. 18:1(n-7) | | 0.82 | 0.81 | 0.77 | | | | 0.83 |
| CE. 18:2(n-6) | 0.91 | | | 0.86 | | | | |
| CE. 18:3(n-6) | | | | | | | | 0.7 |
| CE. 18:3(n-3) | | | | 0.73 | 0.83 | | 0.7 | |
| DAG. 16:0 | | 0.87 | | 0.89 | 0.8 | 0.9 | | |
| DAG. 16:1 | 0.87 | | | 0.91 | 0.92 | 0.9 | | |
| DAG. 18:0 | | | | | | | | |
| DAG. 18:1(n-9) | 0.89 | 0.91 | | | 0.97 | 0.99 | | |
| DAG. 18:1(n-7) | 0.8 | 0.92 | | 0.97 | | 0.95 | | |
| DAG. 18:2(n-6) | 0.9 | 0.9 | | 0.99 | 0.95 | | | |
| DAG. 18:3(n-6) | | | | | | | | |
| DAG. 18:3(n-3) | | | | | | | | |
| FA. 16:0 | | | 0.78 | | | | | 0.83 |
| FA. 16:1(n-7) | | | | | | | | |
| FA. 18:0 | 0.78 | | | | | | | 0.79 |
| FA. 18:1(n-9) | | | | | | | 0.76 | |
| FA. 18:1(n-7) | | | | | | | | |
| FA. 18:2(n-6) | | | | | | | | |
| FA. 18:3(n-6) | | | | 0.76 | | | | |
| FA. 18:3(n-3) | 0.83 | | 0.79 | | | | | |
| PL. 16:0 | | 0.76 | 0.76 | 0.73 | 0.84 | 0.76 | | |
| PL. 16:1(n-7) | 0.76 | | | | 0.78 | | | |
| PL. 18:0 | 0.76 | | | | | 0.9 | | |
| PL. 18:1(n-9) | 0.73 | | | | | | | |
| PL. 18:1(n-7) | 0.84 | 0.78 | | | | 0.7 | | |

TABLE 3-continued

Spearman rank correlations greater than 0.7 among C16 and C18 fatty acids by lipid class based on plasma concentration

| Fatty acid | 16:0 | 16:1(n-7) | 18:0 | 18:1(n-9) | 18:1(n-7) | 18:2(n-6) | 18:3(n-6) | 18:3(n-3) |
|---|---|---|---|---|---|---|---|---|
| PL. 18:2(n-6) | 0.76 | | 0.9 | | 0.7 | | | |
| PL. 18:3(n-6) | | | | | | | | |
| PL. 18:3(n-3) | | | | | | | | |
| TG. 16:0 | | 0.79 | 0.95 | 0.93 | 0.91 | 0.96 | 0.89 | 0.92 |
| TG. 16:1(n-7) | 0.79 | | 0.7 | 0.81 | 0.88 | 0.82 | 0.83 | 0.84 |
| TG. 18:0 | 0.95 | 0.7 | | 0.89 | 0.86 | 0.92 | 0.83 | 0.89 |
| TG. 18:1(n-9) | 0.93 | 0.81 | 0.89 | | 0.91 | 0.94 | 0.93 | 0.92 |
| TG. 18:1(n-7) | 0.91 | 0.88 | 0.86 | 0.91 | | 0.9 | 0.85 | 0.88 |
| TG. 18:2(n-6) | 0.96 | 0.82 | 0.92 | 0.94 | 0.9 | | 0.94 | 0.96 |
| TG. 18:3(n-6) | 0.89 | 0.83 | 0.83 | 0.93 | 0.85 | 0.94 | | 0.93 |
| TG. 18:3(n-3) | 0.92 | 0.84 | 0.89 | 0.92 | 0.88 | 0.96 | 0.93 | |

TABLE 4

Spearman rank correlations greater than 0.7 among C16 and C18 fatty acids by lipid class based on percent concentration

| | Pre-diagnosis (n = 16) | | | | | | | |
|---|---|---|---|---|---|---|---|---|
| Fatty acid | 16:0 | 16:1(n-7) | 18:0 | 18:1(n-9) | 18:1(n-7) | 18:2(n-6) | 18:3(n-6) | 18:3(n-3) |
| CE. 16:0 | | | | | | | | |
| CE. 16:1(n-7) | | | 0.8 | | | −0.75 | | |
| CE. 18:0 | | 0.8 | | | | −0.84 | | |
| CE. 18:1(n-9) | | | | | 0.72 | −0.89 | | |
| CE. 18:1(n-7) | | | | 0.72 | | −0.75 | | |
| CE. 18:2(n-6) | | −0.75 | −0.84 | −0.89 | −0.75 | | | |
| CE. 18:3(n-6) | | | | | | | | |
| CE. 18:3(n-3) | | | | | | | | |
| DAG. 16:0 | | | 0.83 | | | | | |
| DAG. 16:1 | | | | | | | | |
| DAG. 18:0 | 0.83 | | | −0.87 | −0.93 | −0.83 | | |
| DAG. 18:1(n-9) | | −0.87 | | | 0.85 | 0.77 | | |
| DAG. 18:1(n-7) | | −0.93 | 0.85 | | | 0.78 | | |
| DAG. 18:2(n-6) | | −0.83 | 0.77 | 0.78 | | | | |
| DAG. 18:3(n-6) | | | | | | | | |
| DAG. 18:3(n-3) | | | | | | | | |
| FA. 16:0 | | −0.88 | | −0.85 | | −0.71 | | 0.71 |
| FA. 16:1(n-7) | −0.88 | | −0.82 | 0.88 | | 0.82 | | |
| FA. 18:0 | | −0.82 | | | | −0.87 | | |
| FA. 18:1(n-9) | −0.85 | 0.88 | | | | | | −0.75 |
| FA. 18:1(n-7) | | | | | | | | |
| FA. 18:2(n-6) | −0.71 | 0.82 | −0.87 | | | | | |
| FA. 18:3(n-6) | | | | | | | | |
| FA. 18:3(n-3) | 0.71 | | | −0.75 | | | | |
| PL. 16:0 | | | | | | | | |
| PL. 16:1(n-7) | | | | | | | | |
| PL. 18:0 | | | | | | | | |
| PL. 18:1(n-9) | | | | | | | | |
| PL. 18:1(n-7) | | | | | | | | |
| PL. 18:2(n-6) | | | | | | | | |
| PL. 18:3(n-6) | | | | | | | | |
| PL. 18:3(n-3) | | | | | | | | |
| TG. 16:0 | | | | | | −0.79 | | |
| TG. 16:1(n-7) | | | | | | | | |
| TG. 18:0 | | | | −0.74 | −0.76 | | −0.8 | |
| TG. 18:1(n-9) | | | −0.74 | | | | | |
| TG. 18:1(n-7) | | | −0.76 | | | | | |
| TG. 18:2(n-6) | −0.79 | | | | | | | 0.85 |
| TG. 18:3(n-6) | | | −0.8 | | | | | |
| TG. 18:3(n-3) | | | | | | 0.85 | | |

| | At diagnosis (n = 16) | | | | | | | |
|---|---|---|---|---|---|---|---|---|
| Fatty acid | 16:0 | 16:1(n-7) | 18:0 | 18:1(n-9) | 18:1(n-7) | 18:2(n-6) | 18:3(n-6) | 18:3(n-3) |
| CE. 16:0 | | | | | | | | |
| CE. 16:1(n-7) | | | | | | | | |
| CE. 18:0 | | | | | −0.74 | | | |
| CE. 18:1(n-9) | | | | | | | | |
| CE. 18:1(n-7) | | | | | | | | |
| CE. 18:2(n-6) | | | −0.74 | | | | | |
| CE. 18:3(n-6) | | | | | | | | |
| CE. 18:3(n-3) | | | | | | | | |
| DAG. 16:0 | | | 0.76 | −0.74 | | −0.8 | | |
| DAG. 16:1 | | | | | | | | |

TABLE 4-continued

Spearman rank correlations greater than 0.7 among C16 and C18 fatty acids by lipid class based on percent concentration

| | | | | | |
|---|---|---|---|---|---|
| DAG. 18:0 | 0.76 | | −0.88 | −0.83 | −0.94 |
| DAG. 18:1(n-9) | −0.74 | −0.88 | | 0.73 | 0.85 |
| DAG. 18:1(n-7) | | | −0.83 | 0.73 | 0.74 |
| DAG. 18:2(n-6) | −0.8 | | −0.94 | 0.85 | 0.74 |
| DAG. 18:3(n-6) | | | | | |
| DAG. 18:3(n-3) | | | | | |
| FA. 16:0 | | | | | −0.81 |
| FA. 16:1(n-7) | | | | 0.87 | |
| FA. 18:0 | | | −0.84 | | |
| FA. 18:1(n-9) | | | −0.84 | | |
| FA. 18:1(n-7) | | 0.87 | | | |
| FA. 18:2(n-6) | −0.81 | | | | |
| FA. 18:3(n-6) | | | | | |
| FA. 18:3(n-3) | | | | | |
| PL. 16:0 | | | | | |
| PL. 16:1(n-7) | | | | | |
| PL. 18:0 | | | | | |
| PL. 18:1(n-9) | | | | | |
| PL. 18:1(n-7) | | | | | |
| PL. 18:2(n-6) | | | | | |
| PL. 18:3(n-6) | | | | | |
| PL. 18:3(n-3) | | | | | |
| TG. 16:0 | | | | | −0.72 |
| TG. 16:1(n-7) | | | | 0.75 | |
| TG. 18:0 | | | | | |
| TG. 18:1(n-9) | | | | | |
| TG. 18:1(n-7) | | 0.75 | | | |
| TG. 18:2(n-6) | | | | | |
| TG. 18:3(n-6) | −0.72 | | | | |
| TG. 18:3(n-3) | | | | | |

Example 3: Lipoprotein Profiling: Distinct Plasma Lipoprotein Profiles Predict Metabolic Syndrome Lipoprotein particles of different sizes were detected in rhesus monkey blood plasma specimens by NMR spectroscopy using the LipoProfile® test through contract with LipoScience, Inc. Analysis also included chemical detection of total HDL, total LDL, total cholesterol, total triacylglycerol, and CRP, and calculated levels for HDL cholesterol and combined total VLDL and chylomicrons using NMR spectroscopy using the LipoProfile®.

Figure 12:
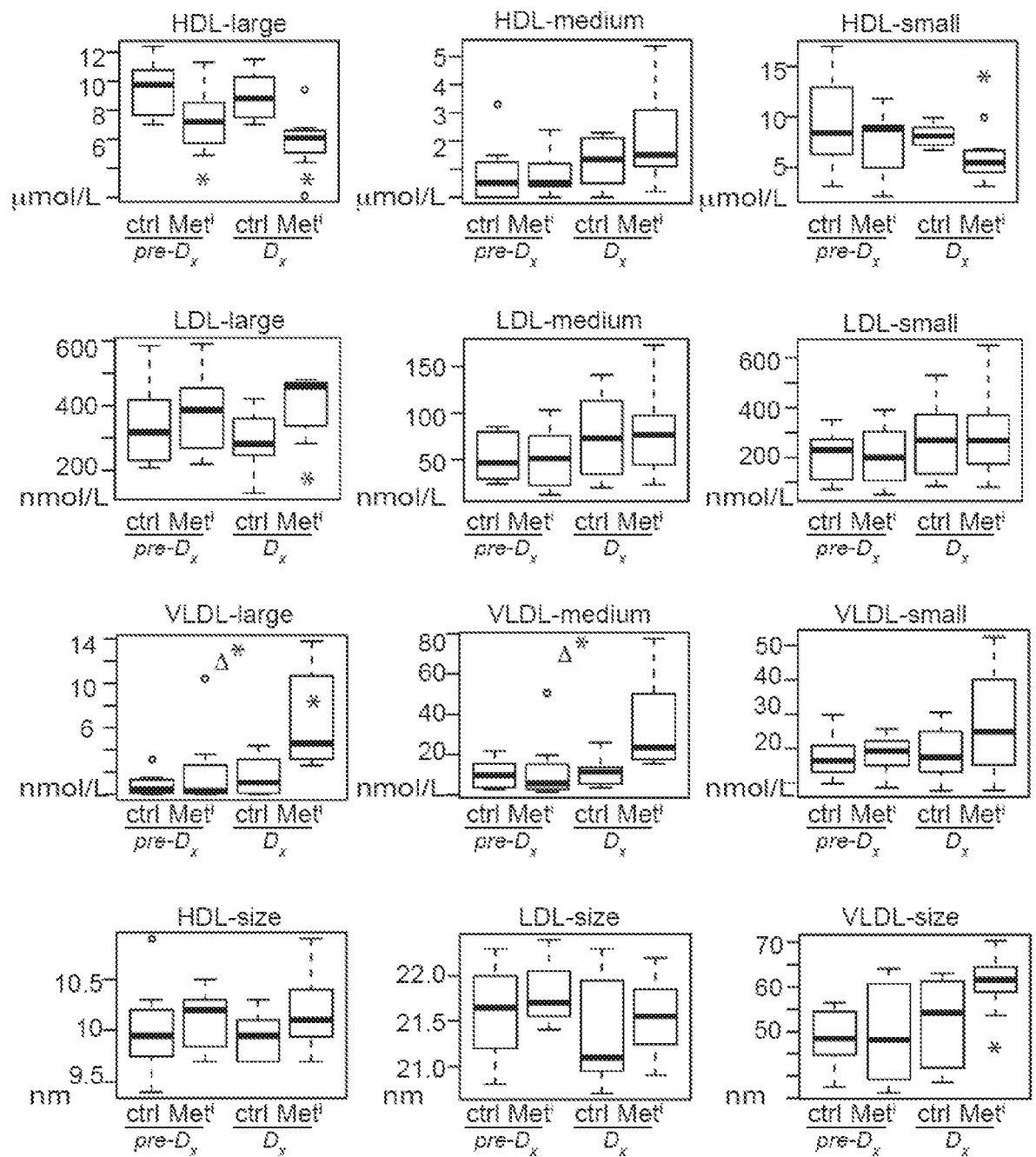
FIG. 12 are graphs illustrating that lipoprotein profiles were altered prior to and during transition to metabolic syndrome. Significant differences in plasma levels of HDL (high density lipoproteins), LDL (low density lipoproteins), VLDL (very low density lipoproteins), and lipoprotein size are shown as medians and IQR in metabolic impaired (Meti) and age- and weight-matched controls (Ctrl) at time of diagnosis (Dx) and two years prior to diagnosis (pre-Dx). Δ*p value<0.05 for difference between the changes for impaired and control animals from two years prior to time of diagnosis.

To understand whether differences in fatty acid composition among the lipid classes were also associated with differences in circulating lipoproteins, NMR-based lipoprotein profiling was conducted using biosamples form healthy and impaired animals. In human studies, low levels of HDL (high density lipoprotein) have been shown to be a hallmark of metabolic syndrome, and an imbalance between circulating levels of HDL relative to LDL and VLDL (low and very low density lipoproteins, respectively) has been associated with systemic inflammation (Rohrer et al., 2004, Curr Opin Lipidol 15: 269-278). Lipoproteins can be further classified by particle size, wherein smaller and denser subclasses of HDL are thought to have greater antioxidant activity and superior anti-inflammatory properties than the larger classes (Chapman, 2007, Diab Vasc Dis Res 4 Suppl 3: S5-8; Kontush & Chapman, 2006, Pharmacol Rev 58: 342-374). At time of diagnosis significant differences in the lipoprotein profiles of control and metabolically-impaired animals were observed that are consistent with human clinical data. Total HDL levels were significantly lower in plasma from impaired animals compared to controls, wherein LDL levels were unchanged, and VLDL and chylomicron levels were significantly higher. Significant differences were also detected in size distribution of the lipoproteins (FIG. 12). The reduction in HDL was shared among large and small particles but not medium particles, and the median overall size of HDL particles was unchanged. Calculated levels of VLDL were significantly larger in impaired animals. Consistent with what is known about human metabolic disease, increases in VLDL (OR 38.4) and triacylglycerols (OR 87.4) in pre-impaired monkeys over the two-year period transitioning to disease onset together predicted glucoregulatory status (94% correct prediction). Total plasma cholesterol levels were not significantly different between groups at either time point. Lasso logistic regression analysis identified two new models for disease prediction from the lipoprotein data (Table 2). The first (Table 2—Model 2) included HDL and IDL lipoproteins, in addition to large HDL particles, and HDL cholesterol (FIG. 5A) that together identified impaired animals two years prior to diagnosis of metabolic disease. The second (Table 2—Model 3) was based on measures at time of diagnosis and included HDL and IDL as before, and small HDL particles and triacylglycerols. These data indicated that the changes in lipoprotein profiles emerged coincident with the development of insulin resistance.

Figure 5:
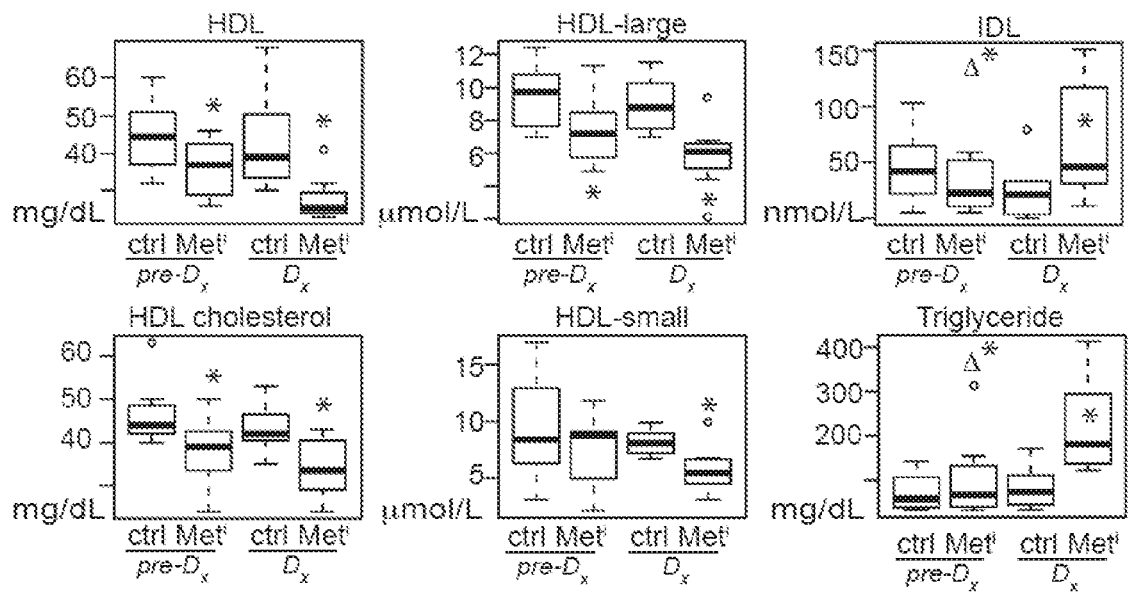
FIGS. 5A-5B illustrate that lipoprotein profiles were altered prior to and during transition to metabolic disease.
Figure 5:
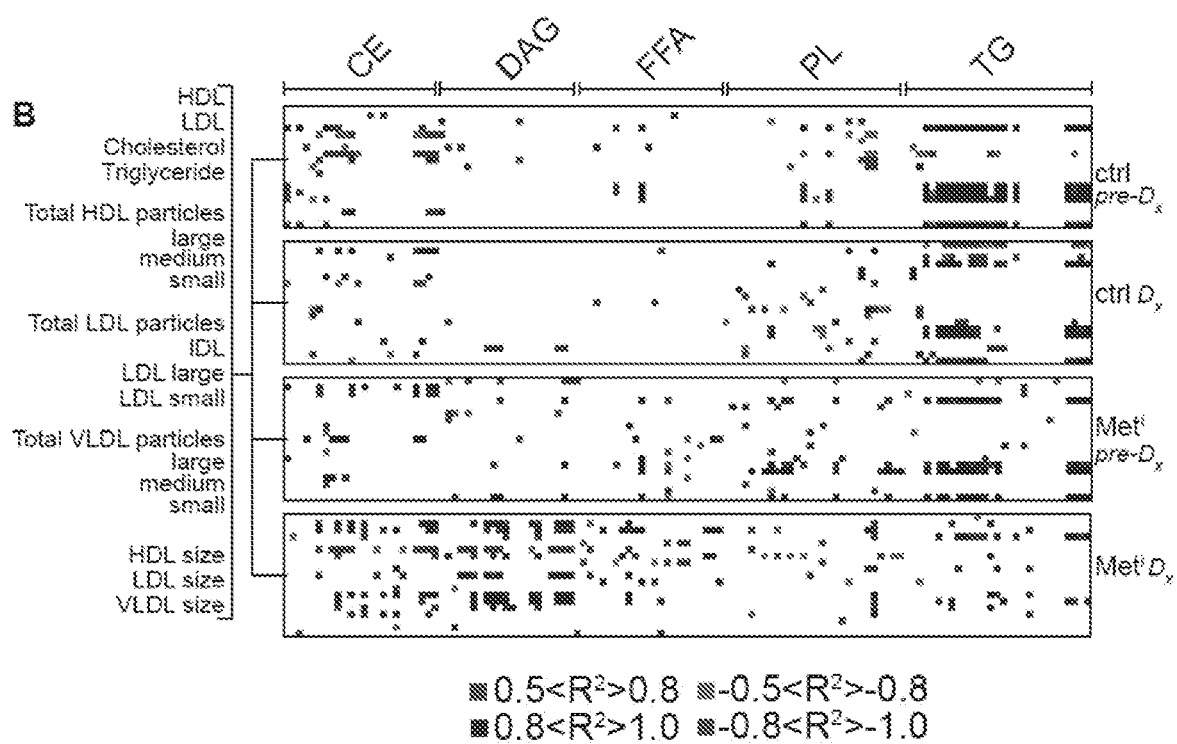
Figure 6:
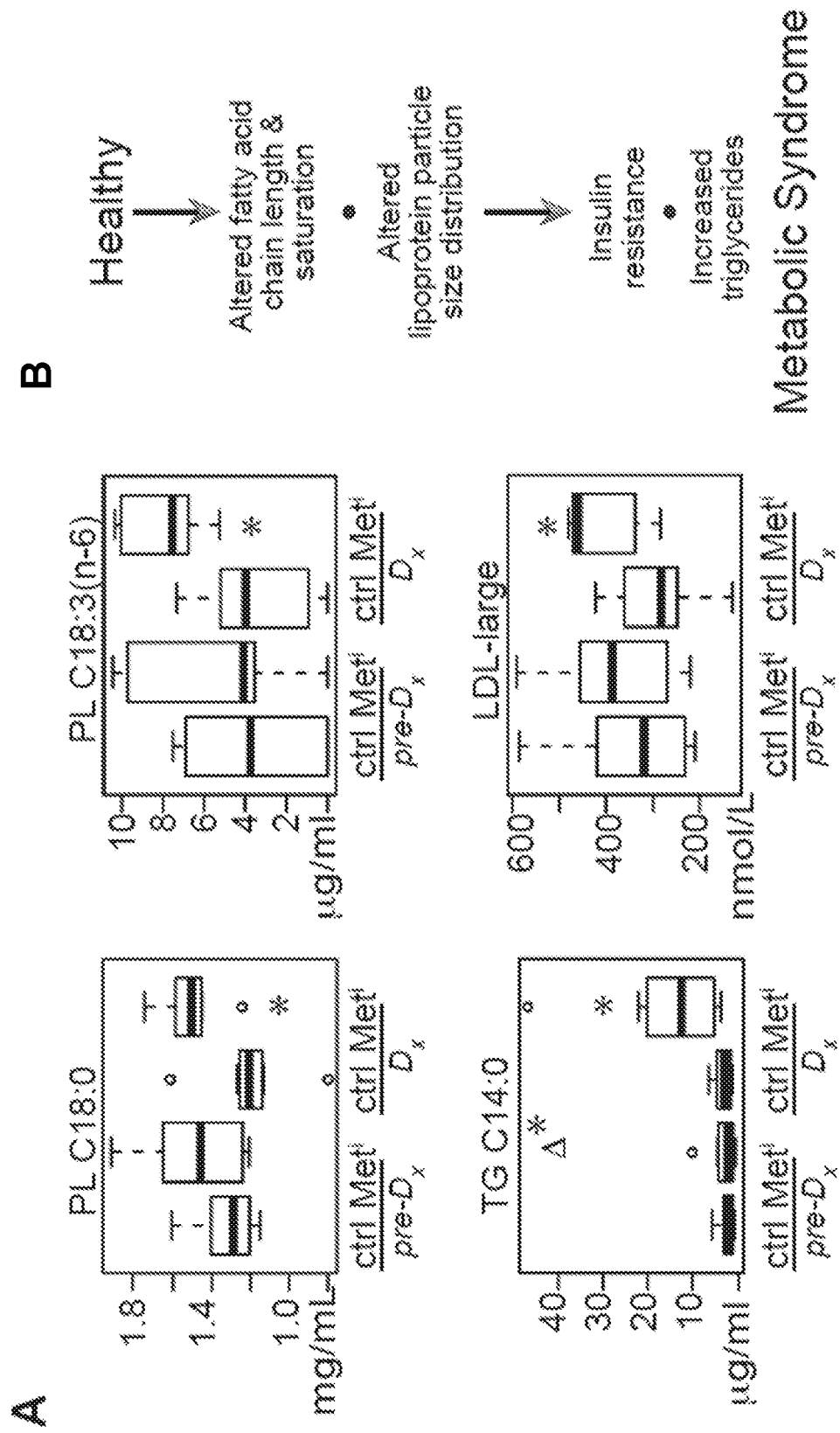
FIGS. 6A-6B illustrate that lipid metabolic index could predict glucoregulatory status.

Correlation analysis was conducted to investigate how changes in lipoproteins related to changes in lipid profiles in progression to disease (FIG. 5B). Strong correlations were identified between VLDLs and TG in healthy animals, wherein VLDL correlated positively and HDLs correlated negatively with CE and negative correlations were also detected between LDL and PL. Two years later negative correlations emerged between HDL and TG, and cholesterol and TG in healthy animals, which suggested an aging effect on lipoproteins and their constituent molecular composition. Distinct correlations were detected in the pre-impaired animals, where plasma VLDL and small LDL correlated negatively with FFA and positively with PL. At time of diagnosis of the impaired animals several new correlations emerged, most notably with DAG. Discrete DAG fatty acid species correlated positively with LDL, cholesterol, and VLDL. The emergence of correlations with cholesterol in impaired animals were particularly interesting as total plasma levels of cholesterol were not different between either group of animals at either time point or between time points. These data suggested that differences in plasma lipid composition during disease transition were related to changes in the lipoprotein profile and that these events occurred early in the progression to metabolic syndrome.

Example 4: Adipokine Analysis

Plasma levels of adipose tissue-derived endocrine factors were also investigated. Adipokines are adipose tissue-secreted peptide signaling molecules that act at the interface of metabolism, inflammation and immune responses (Hotamisligil, 2006, Nature 444: 860-867; Lago et al., 2007, Cytokine Growth Factor Rev 18: 313-325; Ouchi et al., 2011, Nat Rev Immunol 11: 85-97). One such molecule is leptin, which is a multifunctional protein that plays a role in energy balance, glucose homeostasis and immunity its levels correlate positively with adipose tissue mass (Rosen & Spiegelman, 2006, Nature 444: 847-853). In monocytes and macrophages, leptin increases the production of inflammatory cytokines and pro-inflammatory factors (Tilg & Moschen, 2006, Nat Rev Immunol 6: 772-783). Resistin is another molecule that is also pro-inflammatory with hyperglycemic action (Rosen & Spiegelman, 2006, Nature 444: 847-853). Resistin levels are increased in models of obesity and resistin has been implicated in the pathogenesis of obesity associated insulin resistance (Lago et al., 2007, Cytokine Growth Factor Rev 18: 313-325; Tilg & Moschen, 2006, Nat Rev Immunol 6: 772-783). However, plasma levels of leptin and resistin measured by ELISA were not significantly different between groups at either time point (FIG. 1C). Adiponectin is another adipose-derived signaling hormone that has been associated with metabolic dysfunction in human studies (Turer & Scherer, 2012, Diabetologia 55: 2319-2326). In general adiponectin levels correlated negatively with adiposity (Turer et al., 2012, J Clin Endocrinol Metab 97: E982-986) and several studies have shown reduced adiponectin levels in Type II diabetes (Obata et al., 2013, Clin Endocrinol (Oxf) 79: 204-210; Wolfson et al., 2012, Exp Diabetes Res 2012: 250621). ELISA assays were used for these determinations, wherein plasma dilution was optimized for each assay and CV of <0.05 was confirmed for replicate measures. Levels of adiponectin and high molecular weight adiponectin in plasma were measured using a customization of a commercially available ELISA (DY1065, R&D Systems). Briefly, parallel plasma specimens were incubated in absence or presence of 0.27 mg/ml proteinase K (Sigma Chemical Co., St. Louis, Mo.) for 20 mins at 37° C. to remove lower molecular weight isoforms. Selective digestion was confirmed by western blot. Non-digested isoforms were detected according to manufacturer's instructions (having a detection range of 0-4 ng/ml). As practiced in the experiments disclosed herein, divergence from the kit included using an alternate capture antibody specific to intact rhesus adiponectin (digested fragments not detected) (AF1065, R&D Systems). Resistin was detected using ELISA (DY1359, R&D Systems) according to manufacturer's instructions (detection range 0-2 ng/ml). Leptin was detected using ELISA (MBS705354, MyBioSource) according to manufacturer's instructions (detection range 0-2 ng/ml). Specificity of antibodies for rhesus peptides was confirmed by western blot.

Despite the fact that adiposity and abdominal circumference were equivalent in healthy and metabolic impaired animals, adiponectin levels tended to be lower in the impaired animals (p=0.07). Focusing on the mid-age animals only (10-16 years of age, n=5), adiponectin levels were lower (p=0.05) in metabolic impaired animals but a significant effect of age on adiponectin levels was not detected. The high molecular weight (HMW) form of adiponectin was isolated using partial proteolysis to remove the lower molecular weight forms followed by ELISA. Levels of HMW adiponectin were not significantly different between groups at either time point but tended to be lower in impaired animals at time of diagnosis (FIG. 1D). Ratios of HMW to total adiponectin tended to be higher in the impaired animals at diagnosis compared to healthy controls although this did not reach significance.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

The invention claimed is:

1. A method for treating a subject without impaired fasting glucose having a risk for glucoregulatory dysfunction, the method comprising:
  (a) selecting a subject without impaired fasting glucose having a risk for glucoregulatory dysfunction by:
    (i) separating diacylglycerols from a biosample isolated from the subject;
    (ii) determining a respective concentration of each of the plurality of diacylglycerol fatty acid species selected from the separated diacylglycerols, wherein the plurality of diacylglycerol fatty acid species comprise fatty acid chains C16:1, C18:2(n-6), C18:3(n-3), and C20:1(n-7); and
    (iii) identifying the subject as having a risk for the glucoregulatory dysfunction because the respective concentration of each of the plurality of diacylglycerol fatty acid species is either increased or decreased relative to a respective control level or range; and
  (b) administering an effective amount of at least one anti-diabetes compound to the subject.

2. The method of claim 1, wherein the respective concentration of each of the plurality of diacylglycerol fatty acid species in (ii) is determined using gas chromatography.

3. The method of claim 1, wherein the biosample comprises serum or plasma from the subject.

4. The method of claim 1, wherein the glucoregulatory dysfunction is metabolic syndrome, pre-diabetes, or Type II diabetes.

5. The method of claim 1, further comprising determining the concentration of one or more lipoproteins in the biosample.

6. The method of claim 5, wherein the one or more lipoproteins is very low density lipoprotein, wherein an increased concentration of the very low density lipoprotein compared to a relative control level or range identifies a subject at risk for glucoregulatory dysfunction.

7. The method of claim 5, wherein the one or more lipoproteins is a high-density lipoprotein, wherein a decreased concentration of the high-density lipoprotein compared to a relative control level or range identifies a subject at risk for glucoregulatory dysfunction.

* * * * *